United States Patent [19]

Murase et al.

[11] Patent Number: 5,034,112
[45] Date of Patent: Jul. 23, 1991

[54] DEVICE FOR MEASURING CONCENTRATION OF NITROGEN OXIDE IN COMBUSTION GAS

[75] Inventors: Isao Murase, Yokosuka; Akinobu Moriyama, Yokohama; Takao Ito; Akira Shimozono, both of Yokosuka, all of Japan

[73] Assignee: Nissan Motor Company, Ltd., Japan

[21] Appl. No.: 352,580

[22] Filed: May 16, 1989

[30] Foreign Application Priority Data

May 19, 1988 [JP] Japan .................. 63-122707

[51] Int. Cl.$^5$ .................................. G01N 27/58
[52] U.S. Cl. ....................... 204/406; 204/153.14; 204/410; 204/412; 204/425
[58] Field of Search .............. 204/1 N, 410, 412, 425, 204/406, 153.14; 422/98

[56] References Cited

U.S. PATENT DOCUMENTS

| 4,450,065 | 5/1984 | Yamada et al. | 204/412 |
| 4,770,760 | 9/1988 | Noda et al. | 204/425 |
| 4,927,517 | 5/1990 | Mizutani et al. | 204/406 |

Primary Examiner—John F. Niebling
Assistant Examiner—William T. Leader
Attorney, Agent, or Firm—Lowe, Price, LeBlanc & Becker

[57] ABSTRACT

For use on automobiles, the invention provides a compact device for measuring the concentration of a nitrogen oxide in a combustion gas such as an exhaust gas of an internal combustion gas. The device has an ion pumping cell using an oxygen ion conductive solid electrolyte to adjust the partial pressure of oxygen in a gas diffusion chamber and a sensor such as an oxygen concentration cell using a solid electrolyte to detect the partial pressure of oxygen in the chamber. The pumping cell or the concentration cell is provided with a catalyst which decomposes the nitrogen oxide in the diffusion chamber only when the partial pressure of coexisting oxygen is sufficiently low. In the device the current supplied to the pumping cell is measured when the partial pressure of oxygen in the diffusion chamber is low enough for the activity of the catalyst and also when the oxygen partial pressure is made too high, and the concentration of the nitrogen oxide in the gas is computed from the two values of the current and the known relationship between the concentration of oxygen in the gas and the current necessary for keeping each of the high and low partial pressures of oxygen. It is convenient to use a pair of combinations of the pumping cell and the concentration cell to keep the high partial pressure of oxygen in one combination and the low partial pressure of oxygen in the other.

15 Claims, 15 Drawing Sheets

DEVICE FOR MEASURING CONCENTRATION OF NITROGEN OXIDE IN COMBUSTION GAS

BACKGROUND OF THE INVENTION

This invention relates to a device for measuring the concentration of a nitrogen oxide in a combustion gas such as an exhaust gas of an internal combustion engine. A probe part of the device has an ion pumping cell using an oxygen ion conductive solid electrolyte, a catalyst for decomposing the nitrogen oxide and an oxygen partial pressure detector such as a concentration cell using an oxygen ion conductive solid electrolyte.

A chemiluminescence analyzer has been used for measuring the concentrations of nitrogen oxides in exhaust gases of automotive internal combustion engines. The analyzer includes a reaction chamber for reacting nitrogen monoxide with ozone to form nitrogen dioxide by the process represented by the reaction formulas (i), (ii) and (iii).

$$NO + O_3 \rightarrow NO_2(\text{or } NO_2^*) + O_2 \quad (i)$$

$$NO_2^* \rightarrow NO_2 + h\nu \quad (ii)$$

$$NO_2^* + M \rightarrow NO_2 + M^* \quad (iii)$$

where $NO_2^*$ represents $NO_2$ in excited state, $h\nu$ is luminous energy, and M represents the molecule of a coexisting gas.

That is, a portion of nitrogen monoxide turns into nitrogen dioxide in an excited state which is unstable in respect of energy, and the resuming of the normal state of nitrogen dioxide is accompanied by emission of light of wavelengths (0.6–3.0 $\mu$m) in the near-infrared region. This phenomenon is utilized since the intensity of the emitted light is approximately proportional to the concentraion of NO (number of NO molecules) in the gas. In the analyzer, the emitted light is amplified and transformed into an electrical signal by a photomultiplier tube to thereby measure the NO concentration in the sample gas.

Since only the concentration of NO can be determined by this method, usually it is necessary to pass the sample gas first through a converter for reduction (or thermal decomposition) of $NO_2$ to NO. The existence of other substances (in particular carbon dioxide) is obstructive to the emission of light by reason of absorption of a portion of the luminous energy and resultant decrease in the intensity of the emitted light. Since such an unfavorable influence can be reduced by carrying out the aforementioned reaction under very low pressure, the analyzer includes a vacuum pump to maintain a sufficiently low pressure in the reaction chamber.

It is inevitable that the chemiluminescence analyzer including the above described components occupies a large space, and a large amount of electric power is needed to operate those components. Therefore, the analyzer is unsuitable for installation on automobiles or other vehicles though it is useful in bench test.

SUMMARY OF THE INVENTION

It is an object of the present invention to provide a device for measuring the concentration of a nitrogen oxide in a combustion gas such as an exhaust gas of an internal combustion engine, which device is convenient for practical use and so compact as can easily be installed on vehicles such as automobiles.

According to the invention there is provided a device for measuring the concentration of a nitrogen oxide in a combustion gas, the device comprising an electrochemical cell which comprises a member of an oxygen ion conductive solid electrolyte and first and second electrodes attached to the solid electrolyte member, a diffusion rate determining means for diffusing a fraction of the combustion gas, with a predetermined resistance to the gas diffusion, into a space in which the first electrode of the electrochemical cell is exposed, a catalyst which is provided in or in the vicinity of the first electrode of the electrochemical cell and decomposes the nitrogen oxide only when the partial pressure of oxygen coexisting with the nitrogen oxide is lower than a predetermined level, means for supplying a variable DC current to the electrochemical cell to flow in the solid electrolyte between the first and second electrodes to thereby cause migration of oxygen ions in a predetermined direction through the solid electrolyte between the first and second electrodes for adjusting the partial pressure of oxygen in the vicinity of the first electrode, means for detecting the partial pressure of oxygen in the vicinity of the first electrode of the electrochemical cell, means for deciding whether the detected partial pressure of oxygen is lower than the predetermined level or not, a first current measuring means for measuring the current supplied to the electrochemical cell when it is decided that the detected partial pressure of oxygen is not lower than the predetermined level, a second current measuring means for measuring the current supplied to the electrochemical cell when it is decided that the detected partial pressure of oxygen is lower than the predetermined level, and means for computing the concentration of the nitrogen oxide in the combustion gas by using the two current values measured by the first and second current measuring means, respectively, and for each of the currents respectively measured by the first and second current measuring means the relationship between the concentration of oxygen in the gas and the current.

The present invention includes the following modifications of the above stated device.

A nitrogen oxide concentration measuring device comprising first and second electrochemical cells each of which is as stated above, for each of the first and second electrochemical cells a diffusion rate determining means as stated above, a nitrogen oxide decomposing catalyst as stated above and a current supplying means as stated above, a first control means for detecting the partial pressure of oxygen in the vicinity of the first electrode of the first electrochemical cell and controlling the current supplied to the first cell such that the detected partial pressure of oxygen becomes constant and higher than the predetermined level, a first current measuring means for measuring the current supplied to the first electrochemical cell while the partial pressure of oxygen in the vicinity of the first electrode of the first cell is higher than the predetermined level, a second control means for detecting the partial pressure of oxygen in the vicinity of the first electrode of the second electrochemical cell and controlling the current supplied to the second cell such that the detected partial pressure of oxygen becomes constant and lower than the predetermined level, a second current measuring means for measuring the current supplied to the second electrochemical cell while the partial pressure of oxygen in the vicinity of the first electrode of the second cell is lower than the predetermined level, and means for computing the concentration of the nitrogen oxide in the combustion gas by using the two current values measured by the first and second current measuring means, respectively, and for each of the currents respectively measured by the first and second current measuring means the relationship between the concentration of oxygen in the gas and the current.

A nitrogen oxide concentration measuring device comprising first and second electrochemical cells each of which is as stated above, for each of the first and second electrochemical cells a diffusion rate determining means as stated above and a current supplying means as stated above, for the second electrochemical cell a nitrogen oxide decomposing catalyst as stated above, another catalyst which is provided in or in the vicinity of the first electrode of the first electrochemical cell and does not decompose the nitrogen oxide irrespective of the partial pressure of oxygen coexisting with the nitrogen oxide, a first control means for detecting the partial pressure of oxygen in the vicinity of the first electrode of the first electrochemical cell and controlling the current supplied to the first cell such that the detected partial pressure of oxygen remains at a constant level, a first current measuring means for measuring the current supplied to the first electrochemical cell while the partial pressure of oxygen detected by the first control means is at the constant level, a second control means for detecting the partial pressure of oxygen in the vicinity of the first electrode of the second electrochemical cell and controlling the current supplied to the second electrochemical cell such that the detected partial pressure of oxygen becomes constant and lower than the predetermined level, a second current measuring means for measuring the current supplied to the second electrochemical cell while the partial pressure of oxygen detected by the second control means is lower than the predetermined level, and means for computing the concentration of the nitrogen oxide in the gas by using the two current values measured by the first and second current measuring means, respectively, and for each of the currents respectively measured by the first and second current measuring means the relationship between the concentration of oxygen in the gas and the current.

A nitrogen oxide concentration measuring device comprising an electrochemical cell as stated above, a diffusion rate determining means as stated above, a nitrogen oxide decomposing catalyst as stated above, a current supplying means as stated above, a first reference means for producing a first electrical signal which represents a relatively high first reference partial pressure, a second reference means for producing a second electrical signal which represents a relatively low second partial pressure, a control means for detecting the partial pressure of oxygen in the vicinity of the first electrode and controlling the current supplied to the electrochemical cell such that the detected partial pressure of oxygen becomes constant and higher than the predetermined level while the first electrical signal is supplied to the control means and becomes constant and lower than the predetermined level while the second electrical signal is supplied to the control means, a switching means for alternately supplying the first electrical signal and the second electrical signal to the control means at predetermined time intervals, means for measuring the current supplied to the electrochemical cell while the partial pressure of oxygen detected by the control means is higher than the predetermined level and also while the partial pressure of oxygen detected by the control means is lower than the predetermined level, and means for computing the concentration of the nitrogen oxide by using the current value measured by the control means while the detected partial pressure of oxygen is higher than the predetermined level, the current value measured by the control means while the detected partial pressure of oxygen is lower than the predetermined level, and for each of the currents respectively measured under the two different conditions of the partial pressure of oxygen the relationship between the concentration of oxygen in the gas and the current.

An example of the aforementioned nitrogen oxide decomposing catalyst is platinum.

In a device according to the invention, it is suitable to employ a concentration cell using an oxygen ion conductive solid electrolyte as a means for detecting the partial pressure of oxygen in the vicinity of the first electrode of the electrochemical cell which functions as an oxygen ion pumping cell. In that case the ion pumping cell and the concetration cell can be united into a single element which is very small in size and can easily be fitted into an exhaust pipe of an automotive engine. When such a sensor element is used the measurement of the concentration of a nitrogen oxide is accomplished with very good responsiveness. The combination of the ion pumping cell and the concentration cell is almost identical with an oxygen sensor or air/fuel ratio detector already developed for use in the exhaust system of automotive engines and, hence, can be produced at relatively low cost.

The remaining parts of the device are electrical circuits for treatment of signals. Therefore, the entirety of the device is made very compact and can be installed and practically used on automobiles and other vehicles without difficulty. Preparatory to the measurement by using a device of the invention, it suffices to find the relationship between the concentration of oxygen in the gas subject to measurement and the output current of each combination of the pumping cell and the concentration cell, aside from determination of the output of the same combination in a gas containing none of the reactive components of combustion gases.

By a device according to the invention the concentration of any of typical nitrogen oxides such as NO, $NO_2$ and $NO_3$ in a combustion gas can be measured by selecting a catalyst suitable for decomposing the nitrogen oxide to be measured.

When a device according to the invention has two ion pumping cells each combined with an oxygen partial pressure detecting means, it is easy to obtain the two current values to be used by the computing means. When a device according to the invention has only one ion pumping cell the device becomes most compact, and it becomes unnecessary to carefully select two cells having similar characteristics, though a somewhat complicated technique is needed to obtain two current values to be used by the computing means.

DESCRIPTION OF THE PREFERRED EMBODIMENTS

Figure 1:
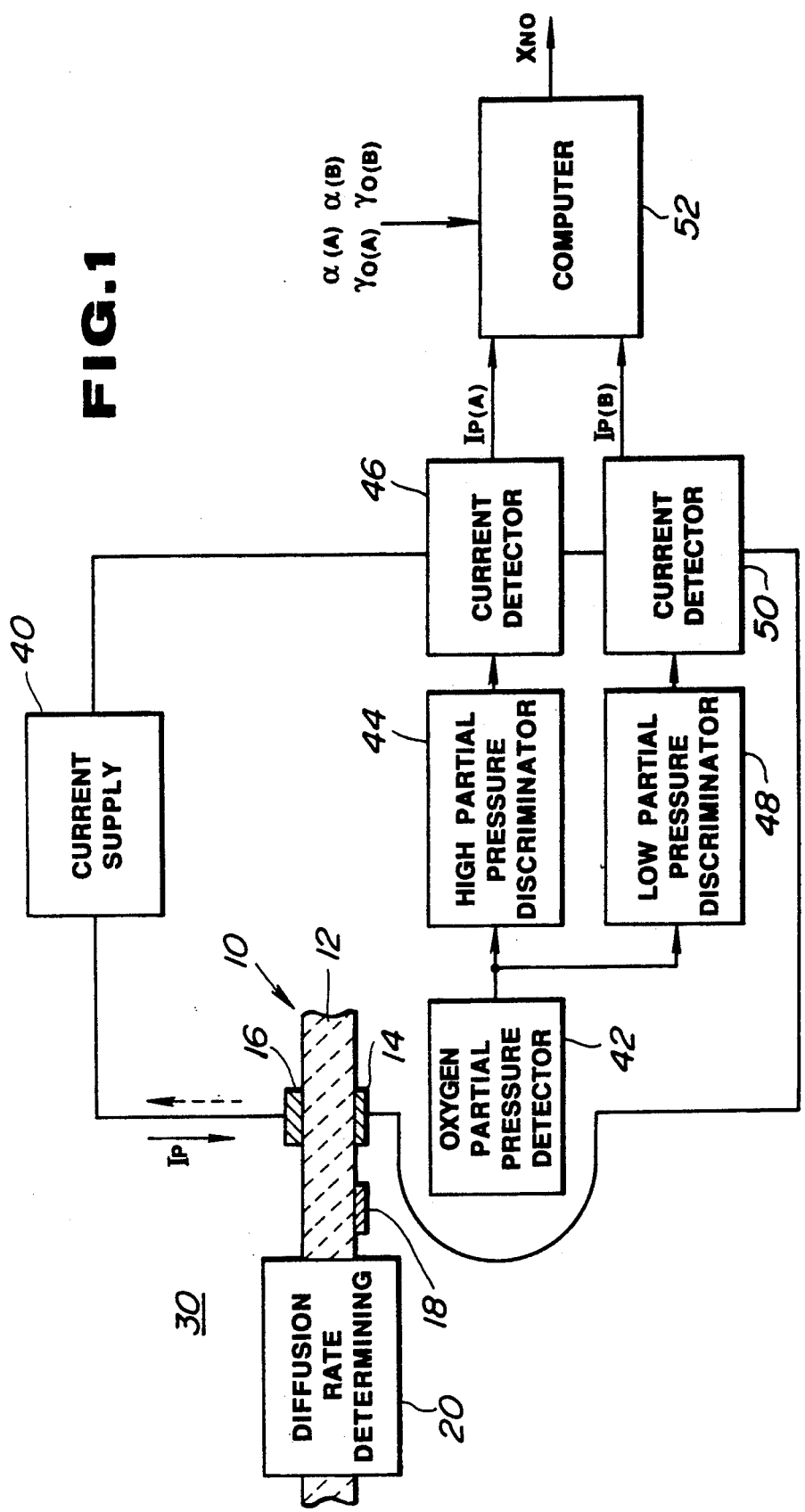
FIGS. 1 to 4 are respectively diagrams of four nitrogen oxide concentration measuring devices according to the invention, the four devices being similar in the principle of operation but different in construction.

FIG. 1 shows a nitrogen oxide concentration measuring device according to the invention. As a probe element the device has an electrochemical cell 10 which is called an oxygen ion pumping cell or simply a pumping cell. Essentially the pumping cell 10 consists of a plate 12 of an oxygen ion conductive solid electrolyte such as zirconia, a first electrode 14 on one side of the solid electrolyte plate 12 and a second electrode 16 on the opposite side of the plate 12. In the vicinity of the first electrode 14 the cell 10 is provided with a catalyst 18 which decomposes a nitrogen oxide (e.g., NO) when the partial pressure of oxygen coexisting with the nitrogen oxide is relatively low but does not decompose the nitrogen oxide when the oxygen partial pressure is relatively high. When the catalyst 18 is an electrically conductive substance it is possible to incorporate the catalyst 18 in the first electrode 14. In combination with the pumping cell 10 there is a gas diffusion rate determining means 20 which provides access to the first electrode 14 and allows a gas subject to measurement to diffuse from an external space 30 into a chamber (not indicated) in which the first electrode 14 and the catalyst 18 are exposed. In using the cell 10 the second electrode 16 may be exposed to the gas in the external space 30.

A current supplying means 40 supplies a variable DC current $I_P$ to the pumping cell 10 so as to flow between the two electrodes 14 and 16 through the solid electrolye plate 12. The flow of the current $I_P$ in the cell 10 causes migration of oxygen ions through the solid electrolyte plate 12 in the direction reverse to the direction of the flow of the current $I_P$. Therefore, the magnitude of oxygen partial pressure in the aforementioned chamber in which the electrode 14 and the catalyst 18 are exposed can be controlled by varying the polarity and intensity of the current $I_P$. The device includes an oxygen partial pressure detecting means 42 to detect the level of oxygen partial pressure in the vicinity of the first electrode 14 of the cell 10, a first discriminating means 44 which can make a decision that the detected oxygen partial pressure is too high for the nitrogen oxide decomposing activity of the catalyst 18, a current measuring means 46 to measure the pumping current $I_P$ when the discrimitating means 44 makes that decision, a second discriminating means 48 which can make a decision that the detected oxygen partial pressure is low enough for the activity of the catalyst 18 and another current measuring means 50 to measure the current $I_P$ when the second discriminating means 48 makes that decision.

The output part of the device is a computing means 52 to compute the concentration of the nitrogen oxide (e.g., NO concentration, $X_{NO}$) in the gas subject to measurement. The current values $I_{P(A)}$ and $I_{P(B)}$ measured by the two measuring means 46 and 50, respectively, are inputted to the computing means 52. Besides, a sensitivity coefficient $\gamma_{O(A)}$ which is indicative of the relationship between the concentration of oxygen in the gas and the measured current $I_{P(A)}$, another sensitivity coefficient $\gamma_{O(B)}$ which is indicative of the relationship between the oxygen concentration and the measured current $I_{P(B)}$ and two zero-state output values $\alpha_{(A)}$ and $\alpha_{(B)}$ which represent the values of the $I_{P(A)}$ and $I_{P(B)}$, respectively, measured when the gas contains no reactive components are input to the computing means 52. The particulars of the computation using these inputs will be described later.

Figure 2:
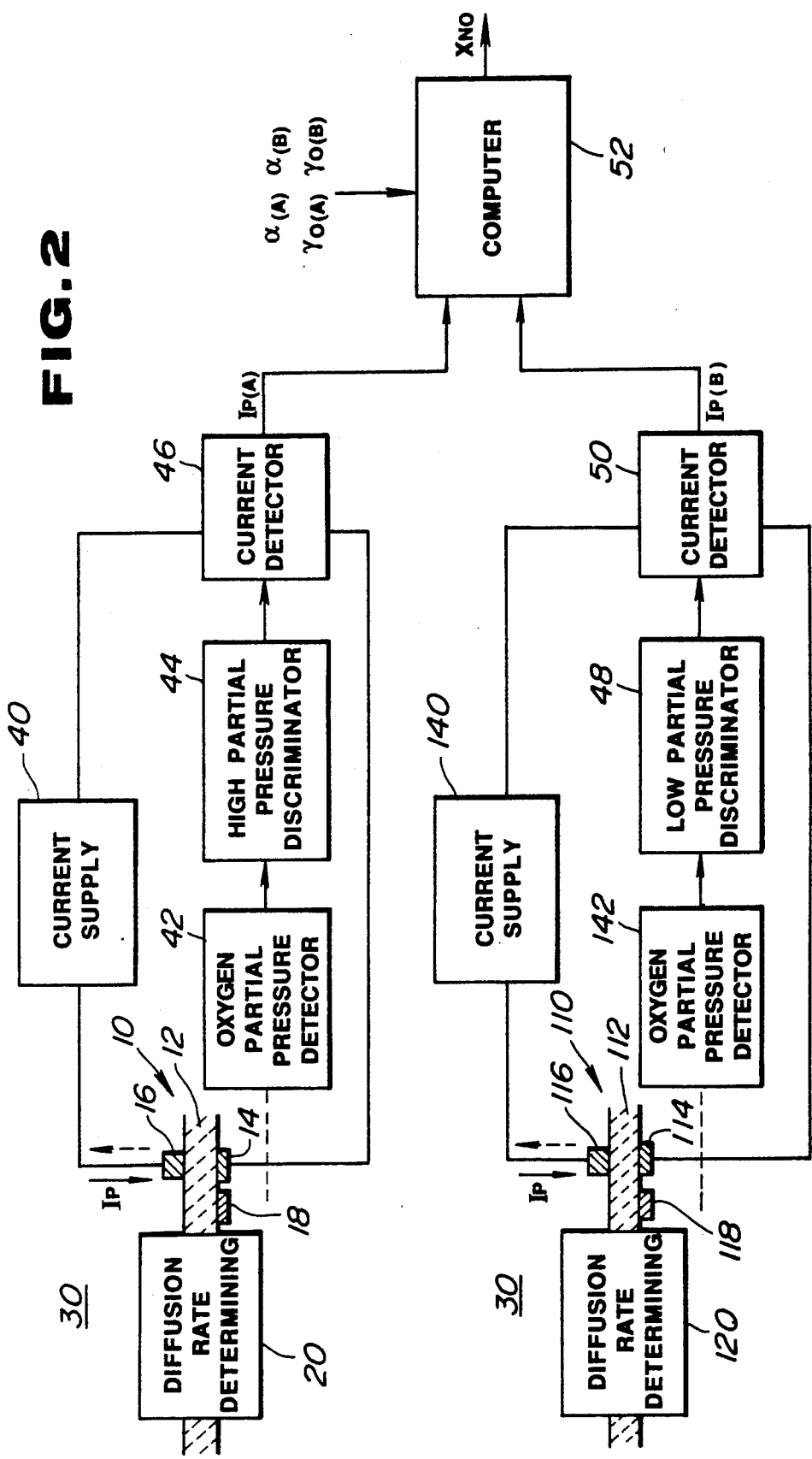

FIG. 2 shows another nitrogen oxide concentration measuring device according to the invention. This device has two pumping cells 10 and 110. The first cell 10 is identical with the cell 10 in FIG. 1 and is provided with the gas diffusion rate determining means 20 described with reference to FIG. 1. The second cell 110 is identical in construction with the first cell 10. That is, the second cell 110 has an oxygen ion conductive solid electrolyte plate 112, a first electrode 114 and a second electrode 116 corresponding to the elements 12, 14 and 16 of the first cell 10, respectively, and in or in the vicinity of the electrode 114 is provided with a nitrogen oxide decomposing catalyst 118 which is active when the partial pressure of oxygen coexisting with the nitrogen oxide is relatively low. For the electrode 114 of the second cell 112 there is a gas diffusion rate determining means 120 corresponding to the means 20 for the first cell 10.

In combination with the first pumping cell 10, the device has the current supplying means 40, oxygen partial pressure measuring means 42, first discriminating means 44 and current measuring means 46 described with reference to FIG. 1. In combination with the second cell 110, the device has a current supply means 140 corresponding to the means 40, an oxygen partial pressure measuring means 142 corresponding to the means 42, the second discriminating means 48 described with reference to FIG. 1 and the current measuring means 50 described with reference to FIG. 1. Therefore, the outputs $I_{P(A)}$ and $I_{P(B)}$ of the two current measuring means 46 and 50 are similar to $I_{P(A)}$ and $I_{P(B)}$ in FIG. 1. The device of FIG. 2 has the nitrogen oxide concentration computing means 52 described with reference to FIG. 1.

Figure 3:
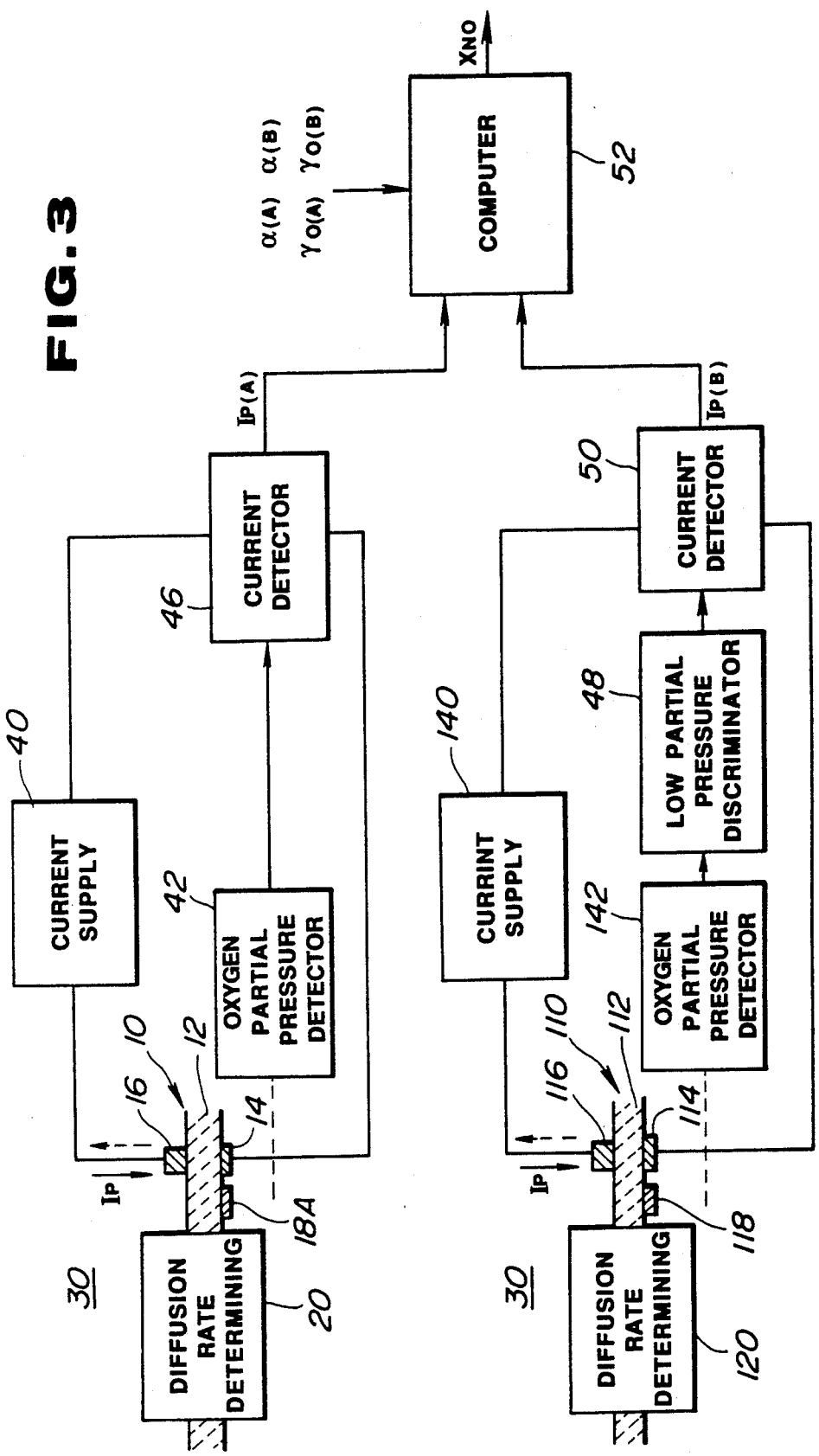

FIG. 3 shows a modification of the device of FIG. 2. The point of modification is that the electrode 14 of the first pumping cell 10 is provided with a catalyst 18A which does not decompose any nitrogen oxide irrespective of the level of partial pressure of oxygen coexisting with the nitrogen oxide. Because of the change in this point, the device of FIG. 3 has no counterpart of the first discriminating means 44 in FIG. 2 (which makes a decision that the partial pressure of oxygen is too high) precedent to the current measuring means 46 for the first pumping cell 10. In the device of FIG. 3 the second pumping cell 110, including the catalyst 118 which decomposes a nitrogen oxide when the partial pressure of coexisting oxygen is relatively low, and the combined means 140, 142, 48 and 50 are identical with the counterparts in FIG. 2. The output part of the device is the computing means 52 described hereinbefore.

Figure 4:
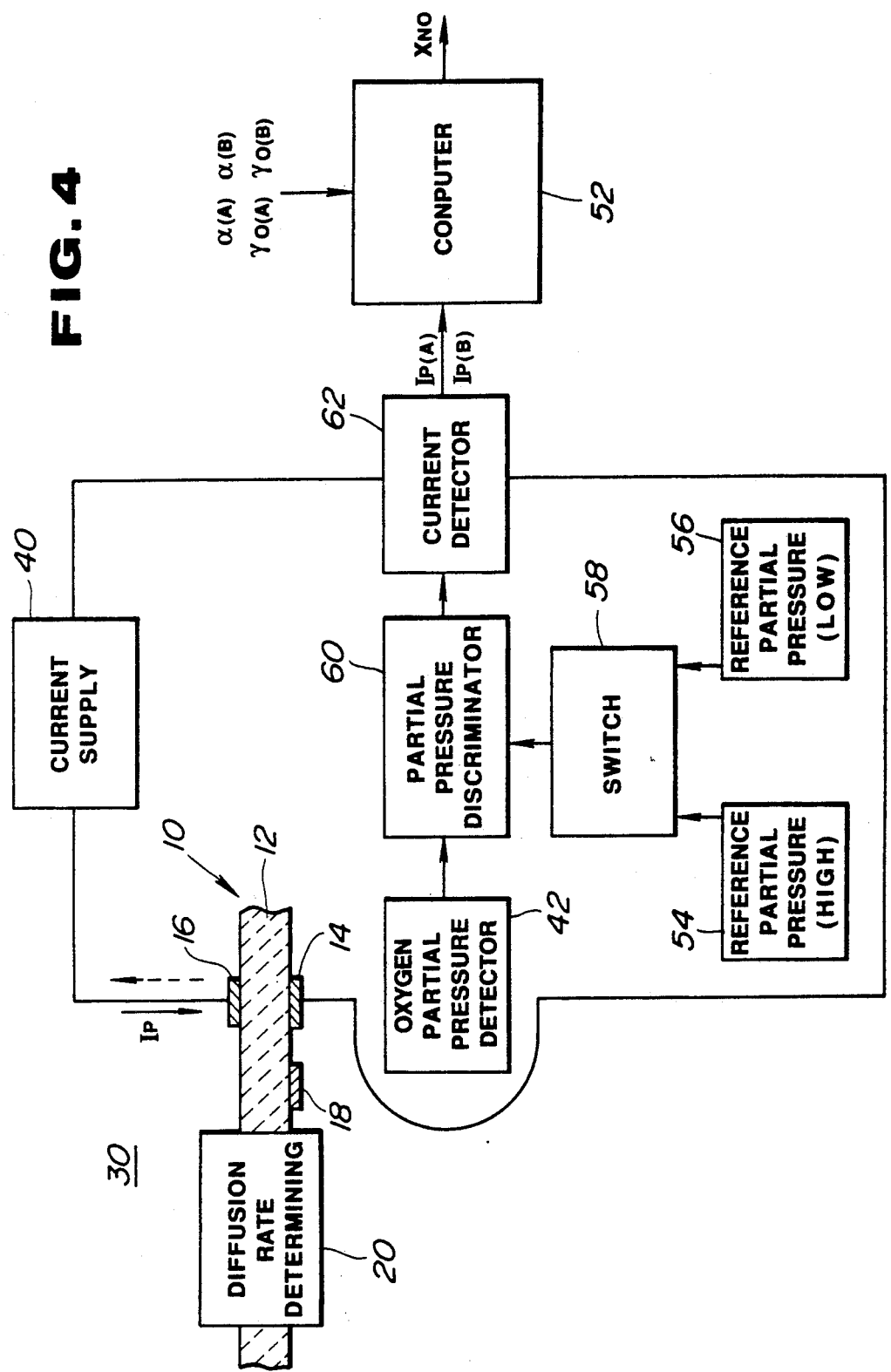

FIG. 4 shows a modification of the device of FIG. 1. This device has the single pumping cell 10 including the catalyst 18, gas diffusion rate determining means 20, current supplying means 40 and oxygen partial pressure measuring means 42 described with reference to FIG. 1. The device includes a reference oxygen partial pressure setting means 54 for producing a signal representing a predetermined and relatively high partial pressure of oxygen as a first reference partial pressure, another reference oxygen partial pressure setting means 56 for producing a signal representing a predetermined and relatively low partial pressure of oxygen as a second reference partial pressure, a switching means 58 for alternately outputting the two signals respectively produced by the two partial pressure setting means 54 and 56 at predetermined time intervals, and a discriminating means 60 to which the output of the switching means 58 is input. The discriminating means 58 repeatedly makes a decision whether the partial pressure of oxygen measured by the measuring means 42 is too high for the nitrogen oxide decomposing activity of the catalyst 18 or low enough for the activity of the catalyst 18 by comparing the measured partial pressure with the high or low reference partial pressure supplied from the switching means 58. Each time such a decision is made a current measuring means 62 measures the pumping current $I_P$ flowing in the cell 10 to put out a current value $I_{(A)}$ when the measured partial pressure of oxygen is too high and another current value $I_{P(B)}$ when the partial pressure of oxygen is low enough. That is, the two current values $I_{P(A)}$ and $I_{P(B)}$ are alternately put out at the aforementioned time intervals. Also in this device these current values $I_{P(A)}$ and $I_{P(B)}$ are used in the computing means 52 for computing the concentration of the nitrogen oxide.

The theory of the measurement of nitrogen oxide concentrations by the present invention will be described with reference to FIGS. 5 to 10. By way of example, the object of measurement is assumed to be nitrogen monoxide NO.

Figure 5:
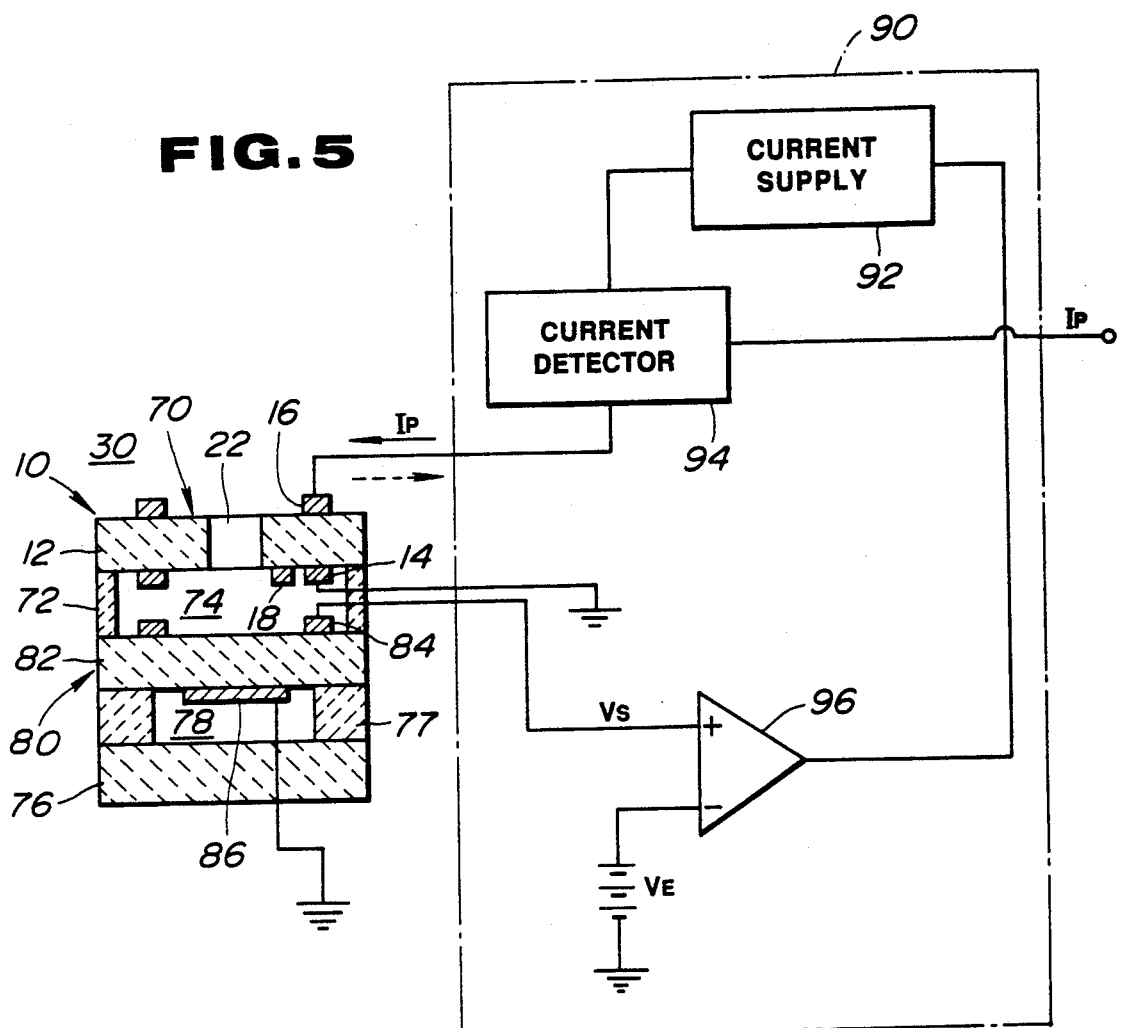
FIG. 5 is a schematic, partly sectional and partly diagrammatic illustration of a sensor which is used in a device according to the invention and consists of a sensor element and a control circuit.

FIG. 5 shows a gas sensor element 70 used in this invention and a control circuit 90 for operating the sensor element 70. The sensor element 70 is a combination of an oxygen ion pumping cell 10 and an oxygen concentration cell 80 which will be called a sensing cell. The pumping cell 10 has a plate 12 of an oxygen ion conductive solid electrolyte such as zirconia, and the sensing cell 80 too has a plate 82 of an oxygen ion conductive solid electrolyte such as zirconia. The two solid electrolyte plates 12 and 82 are held opposite to and spaced from each other by a frame-like spacer 72. The solid electrolyte plate 12 of the pumping cell 70 is formed with a through-hole 22 in a central area to provide access to the space 74 defined between the two plates 12 and 82. The hole 22 serves as the gas diffusion rate determining means 20 in FIG. 1, and the space 74 is used as a gas diffusion chamber. The solid electrolyte plate 12 of the pumping cell 10 is provided with an annular first electrode 14 on its inner surface and an annular second electrode 16 on its outer surface. In or in the vicinity of the first electrode 14 the pumping cell 10 is provided with a catalyst 18 which decomposes (reduces) nitrogen monoxide NO when the partial pressure of oxygen in the gas diffusion chamber 76 is sufficiently low. The solid electrolyte plate 82 of the sensing cell 80 is provided with an annular electrode 84 (called a measurement electrode) on the surface exposed in the gas diffusion chamber 74 and another electrode 86 (called a reference electrode) on the opposite surface. The sensing cell 80 is held spaced from a shield plate 76 by a frame-like spacer 77, and the atmospheric air is introduced into a chamber 78 formed between the two plates 76 and 82.

A current supplying means 92 supplies a variable DC current $I_P$ to the pumping cell 10 to flow between the two electrodes 14 and 16 through the solid electrolyte plate 12. By controlling the polarity and intensity of the pumping current $I_P$ it is possible to desirably vary the partial pressure of oxygen in the gas in the vicinity of the first electrode 14. For example, when an exhaust gas of an automotive engine operated with a lean mixture is introduced into the gas diffusion chamber 74 it is possible to render the oxygen partial pressure in the vicinity of the electrode 14 equivalent to the oxygen partial pressure in an exhaust gas produced by combustion of a stoichiometric air/fuel mixture by flowing the current $I_P$ in the direction of the arrow in solid line to thereby pump out excess $O_2$ contained in the exhaust gas. When the exhaust gas admitted into the chamber 74 is produced by combustion of a rich mixture and hence contains combustible components such as CO and $H_2$, the oxygen partial pressure in the vicinity of the electrode 14 can be raised to a desired level by flowing the current $I_P$ in the direction of the arrow in broken line to thereby pump $O_2$ (formed mainly by the reduction of $CO_2$ at the electrode 16) into the gas diffusion chamber 74.

The height of the gas diffusion chamber 74 is so small that the oxygen partial pressure in the vicinity of the measurement electrode 84 is approximately equivalent to that in the vicinity of the electrode 14 of the pumping cell 10. According to the ratio of the oxygen partial pressure $P_r$ at the reference electrode 86 and the oxygen partial pressure $P_m$ at the measurement electrode 84, the sensing cell (concentration cell) 80 generates an electromotive force E, which is given by the Nernst equation.

$$E = (RT/4F)\log_e(P_r/P_m) \qquad (1)$$

where R is the gas constant, F is the Faraday constant and T is the absolute temperature of the sensor element.

Figure 6:
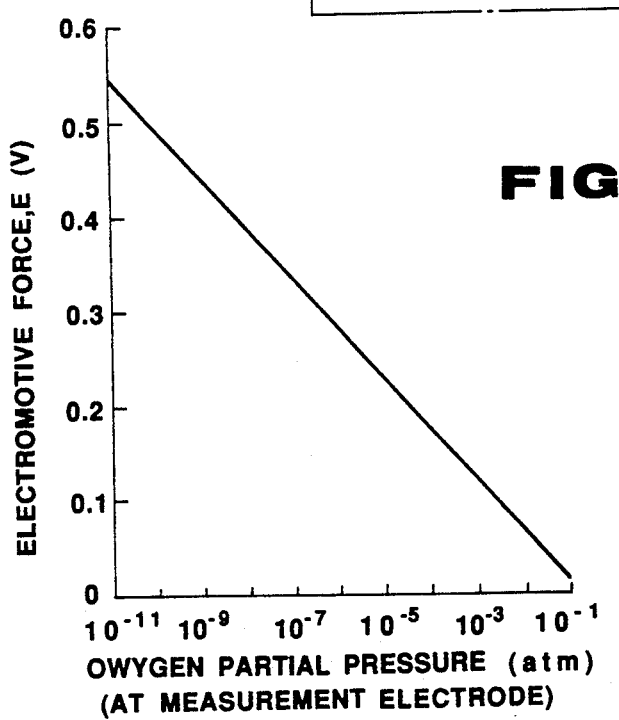
FIG. 6 is a chart showing the output characteristic of an oxygen concentration cell in the sensor element of FIG. 5.

For example, when the air is used as the reference gas to which the reference electrode 86 is exposed (that is, $P_r$ is about 0.209 atm) and the temperature T is 1073° K., the relationship between the oxygen partial pressure $P_m$ at the measurement electrode 84 and the electromotive force E becomes as shown in FIG. 6.

In the sensor element 70 in FIG. 5 the sensing cell 80 serves as a means to measure the oxygen partial pressure in the vicinity of the electrodes 14 and 84. In FIG. 5 the electromotive force generated by the sensing cell 80 is indicated as the output voltage $V_S$. The control circuit 90 in FIG. 5 is constructed so as to keep the output voltage $V_S$ of the sensing cell 80 at a predetermined constant value, $V_E$, by controlling the intensity of the pumping current $I_P$. In the control circuit 90 the reference voltage $V_E$ and the output voltage $V_S$ are inputted to a differential amplifier 96, which acts as a comparator and produces an output representing the amount of deviation of the output voltage $V_S$ from the reference voltage $V_E$. The output of the differential amplifier 96 is provided to the current supplying means 92 as a feedback signal to increase or decrease the pumping current $I_P$ until the output voltage $V_S$ becomes equal to the reference voltage $V_E$. The intensity of the current $I_P$ necessary for keeping the output voltage $V_S$ equal to the reference voltage $V_E$ is measured by a current measuring means 94 to use as the output of the sensor unit. The thus produced output ($I_P$) of the sensor unit has a known relationship to the concentration of oxygen in the exhaust gas in which the sensor element 70 is disposed. Accordingly the combination of the sensor element 70, except the catalyst 18, and the control circuit 90 is useful as an air/fuel ratio detector for use in exhaust gases of automotive engines operated with either a lean mixture or a rich mixture as shown, for example, in U.S. Pat. No. 4,450,065.

Figure 7:
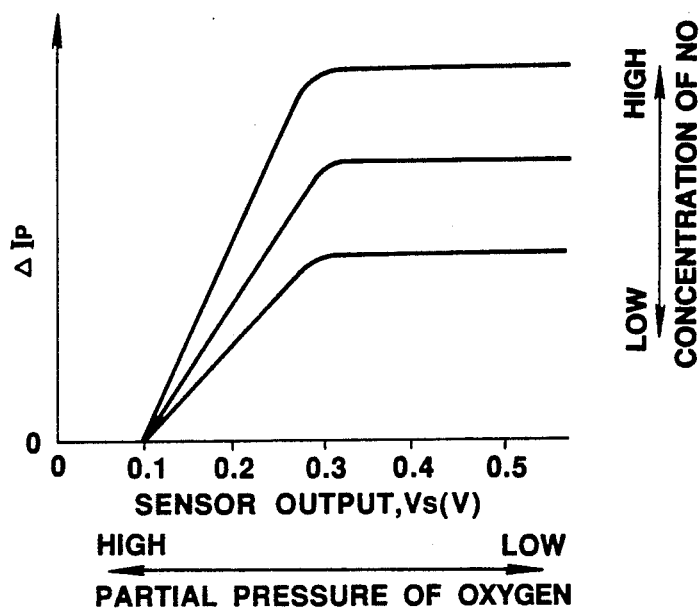
FIG. 7 is a chart showing changes in the relationship between the output voltage of the oxygen concentration cell and the output current of the sensor of FIG. 5 with the concentrations of nitrogen monoxide in gases admitted into the sensor element.

FIG. 7 shows the relationship between the output voltage $V_S$ of the sensing cell 80 and the current $I_P$ (its absolute value in the strict sense) as the output of the sensor unit of FIG. 5. Since the sensor element 70 includes the catalyst 18 which decomposes NO when the partial pressure of oxygen in the gas existing in the vicinity of the catalyst 18 and the electrode 14 is sufficiently low but does not decompose NO when the oxygen partial pressure is relatively high, the output current $I_P$ corresponding to a given value of the voltage $V_S$ increases as the concentration of NO in the gas existing in the vicinity of the electrode 14 increases. That is, the output current $I_P$ depends on the NO concentration too.

Platinum and rhodium are good examples of catalysts which decompose NO when the partial pressure of coexisting oxygen is low. Platinum is very suitable as the electrode material for both the pumping cell 10 and the sensing cell 80. When the electrode 14 of the pumping cell 10 and/or the measurement electrode 84 of the sensing element 80 is made of platinum it is unnecessary to separately provide the catalyst 18.

Figure 8:
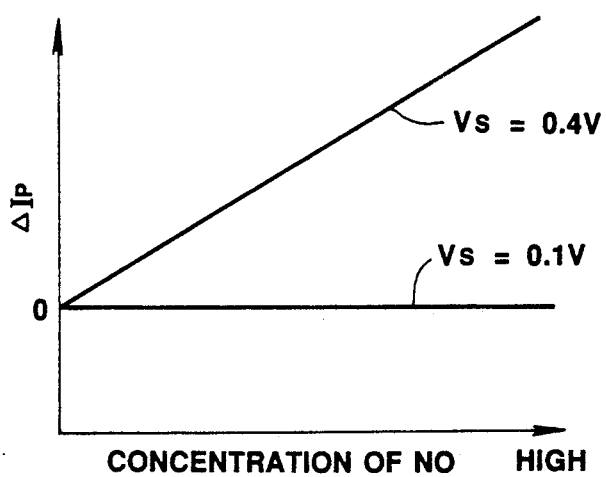
FIG. 8 is a chart derived from the chart of FIG. 7 to show the relationship between the nitrogen monoxide concentration and the output current.
Figure 9:
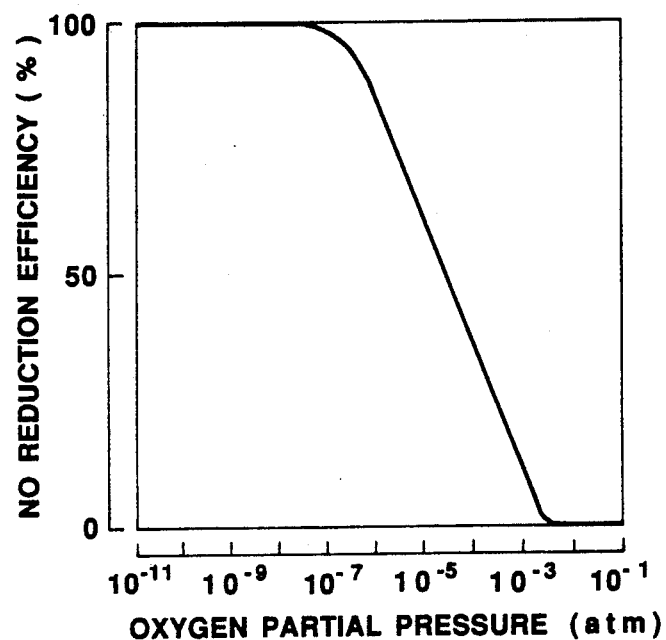
FIG. 9 is a graph showing the dependence of the efficiency of a nitrogen monoxide decomposing catalyst on the partial pressure of oxygen coexisting with nitrogen monoxide.

With respect to one value of the voltage $V_S$ (0.4 V for example) which indicates a relatively low partial pressure of oxygen in the gas diffusion chamber 74 and another value of $V_S$ (0.1 V for example) which indicates a relatively high partial pressure of oxygen in the chamber 74, the relationship between the NO concentration in the gas in the chamber 74 and the output current $I_P$ becomes as shown in FIG. 8 by transformation of the chart of FIG. 7. That is, the output current $I_P$ increases in proportion to the NO concentration when $V_S$ is 0.4 V but remains constant irrespective of the NO concentration when $V_S$ is 0.1 V. In the latter case the reason for the independence of the current $I_P$ on the NO concentration is that the oxygen partial pressure in the chamber 74 is so high that the catalyst 18 cannot decompose (reduce) NO. The relationship between the oxygen partial pressure and the NO reducing efficiency of the catalyst 18 varies according to the material of the catalyst. For example, in the case of platinum the relationship is as shown in FIG. 9. As can be seen, the NO reducing efficiency of the platinum catalyst becomes zero when the oxygen partial pressure is about $10^{-2}$ atm or higher (then the output voltage $V_S$ becomes about 0.1 V). The efficiency of the platinum catalyst becomes very high when the oxygen partial pressure is as low as $10^{-8}$ to $10^{-9}$ atm (then the voltage $V_S$ becomes about 0.4 V).

The charts of FIGS. 7 and 8 show that when the pumping current $I_P$ is varied so as to keep the output voltage $V_S$ of the sensing cell 80 constant at an appropriately chosen value such as 0.4 V the value of $I_P$ in the equilibrated state is proportional to the NO concentration in the gas subject to measurement. The constant value of $V_S$ is not limited to 0.4 V and may be any value in the region (in FIG. 7) wherein a small change in $V_S$ causes little change in $I_P$.

Using the Nernst equation, the dependence of the current $I_P$ as the output of the sensor unit of FIG. 5 on the concentration, X, of a specific component of the exhaust gas subject to measurement is given by the following equation (2).

$$I_P = (nF/RT)P \cdot D(A/L)X \tag{2}$$

where n is the number of electric charges in the electrode reaction, P is the gas pressure, A is the sectional area of the gas diffusion chamber 74 effective for diffusion of gases, L is the height of the chamber 74 effective for diffusion of gases, D is a gas diffusion coefficient determined by the dimensions of the gas admitting hole 22, and F, R and T are as defined with respect to the equation (1).

The equation (2) also shows that the current $I_P$ as the output of the sensor unit is proportional to the concentration X of a component of the exhaust gas, such as NO in the chart of FIG. 8.

Figure 10:
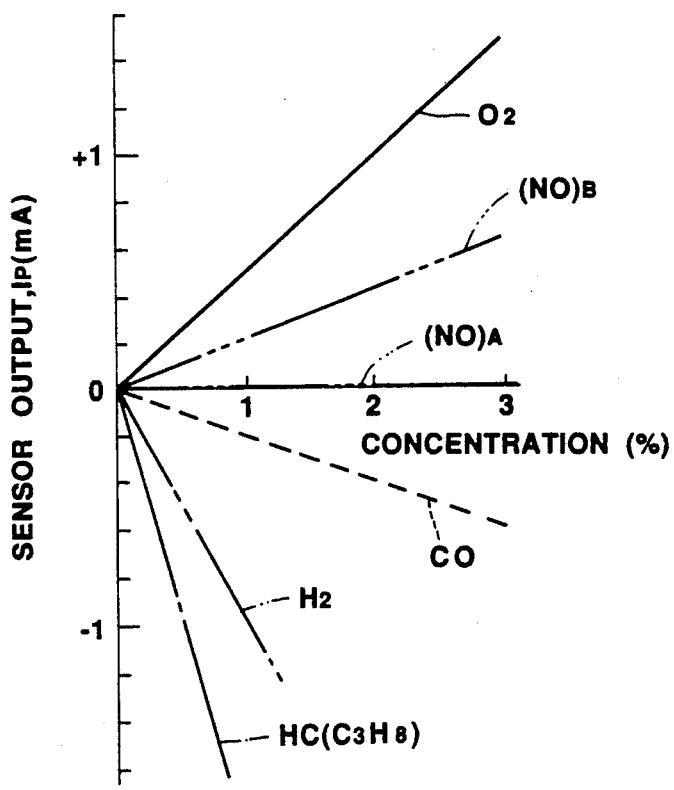
FIG. 10 is a graph showing variations in the output current of the sensor of FIG. 5 with concentrations of several components of combustion gases admitted into the sensor element.

In theory, the composition of the exhaust gas of an internal combustion engine can be determined from combustion reaction (including water gas reaction) formulas with proviso that the composition of the fuel is known. Using model gases of the compositions determined from combustion reaction formulas, experiments were made on the relationship between the concentration of each of the reactive components of the exhaust gases ($O_2$, CO, $H_2$, NO, HC) and the current $I_P$ (its absolute value in the strict sense) as the output of the sensor unit of FIG. 5. The results were as shown in FIG. 10, wherein the curve (NO)$_A$ was obtained when the reference voltage $V_E$ was 0.1 V and the curve (NO)$_B$ when $V_E$ was 0.4 V. It is seen that for each component of the exhaust gases the output current $I_P$ is proportional to the concentration of that component (when both the gas temperature and gas pressure are constant). For each component of the exhaust gases the ratio of the current $I_P$ as the output of the employed sensor unit to the concentration of that component is a constant, which is called a sensitivity coefficient in this invention. The unit of each sensitivity coefficient is mA/%. The chart of FIG. 10 indicates that the sensitivity coefficient for NO (in the case of (NO)$_B$) is about ½ of the sensitivity coefficient for $O_2$.

Thus, it is understood that the current $I_P$ as the output of the sensor unit has a definite relation to the concentrations of several components of the exhaust gases, viz. concentrations of $O_2$, HC and NO when a lean mixture is used and concentrations of CO, $H_2$, HC and NO when a rich mixture is used.

The concentrations of other components of the exhaust gases such as $N_2$, $CO_2$ and $H_2O$ do not affect the output current $I_P$ since for each of these components n (number of electric charges in the electrode reaction) in the equation (2) is zero.

From the above described fundamental characteristics of the sensor unit, the output current $I_P$ can be expressed by the following equation (3) over the entire range of air/fuel ratio.

$$I_P = \gamma_O \cdot X_O + \gamma_{CO} \cdot X_{CO} + \gamma_H \cdot X_H + \gamma_{HC} \cdot X_{HC} + \gamma_{NO} \cdot X_{NO} + \alpha \quad (3)$$

where $X_O$, $X_{CO}$, $X_H$, $X_{HC}$ and $X_{NO}$ are the concentrations (%) of $O_2$, CO, $H_2$, HC and NO in the exhaust gas subject to measurement, respectively, $\gamma_O$, $\gamma_{CO}$, $\gamma_H$, $\gamma_{HC}$ and $\gamma_{NO}$ are sensitivity coefficients (mA/%) for $O_2$, CO, $H_2$, HC and NO, respectively, and $\alpha$ is the value of $I_P$ when $X_O$, $X_{CO}$, $X_H$, $X_{HC}$ and $X_{NO}$ are all 0%.

The equation (3) holds when the reference voltage $V_E$ in FIG. 5 is 0.4 V. When $V_E$ is 0.1 V, the equation (3) is modified by deleting the fifth term, $\gamma_{NO} \cdot X_{NO}$.

For explanation of the computation of the concentration of NO in the exhaust gas subject to measurement, it is assumed that a pair of sensor units each of which is as shown in FIG. 1 are used jointly. One sensor unit is referred as sensor A, and the other as sensor B. In the sensor A the reference voltage $V_E$ is set at 0.1 V, whereas in the sensor B $V_E$ is set at 0.4 V. In the following equations the subscripts (A) and (B) represent the sensor A and the sensor B, respectively.

As mentioned above with respect to the equation (3), the output $I_{P(A)}$ of the sensor A is given by the following equation (4).

$$I_{P(A)} = \gamma_{O(A)} \cdot X_O + \gamma_{CO(A)} \cdot X_{CO} + \gamma_{H(A)} \cdot X_H + \gamma_{HC(A)} \cdot X_{HC} + \alpha_{(A)} \quad (4)$$

The output $I_{P(B)}$ of the sensor B is given by the equation (5).

$$I_{P(B)} = \gamma_{O(B)} \cdot X_O + \gamma_{CO(B)} \cdot X_{CO} + \gamma_{H(B)} \cdot X_H + \gamma_{HC(B)} \cdot X_{HC} + \gamma_{NO(B)} \cdot X_{NO} + \alpha_{(B)} \quad (5)$$

The equation (5) differs from the equation (4) only in that the fifth term, $\gamma_{NO(B)} \cdot X_{NO}$, is added and that the value of $\alpha_{(B)}$ (zero-state output) differs from the value of $\alpha_{(A)}$. The values of $\alpha_{(A)}$ and $\alpha_{(B)}$ can be determined by testing prior to actual measurement.

It seems that the NO concentration, $X_{NO}$, can be determined by making a subtraction between the equations (5) and (4). However, for the following reasons it is impossible to actually determine the NO concentration by simply calculating the difference between the outputs of the sensors A and B, $I_{P(B)} - I_{P(A)}$. The sensitivity coefficients of the respective sensors for $O_2$, CO, $H_2$ HC and NO are roughly as shown in the following table. That is, the sensitivity coefficient for NO, $\gamma_{NO(B)}$, takes a very small value. Besides, the concentration of NO in the exhaust gas subject to measurement is very low ($10^2$–$10^3$ ppm) compared with the concentrations of $O_2$, CO and $H_2$. Therefore, an actual change in the sensor output current $I_{P(B)}$ attributed to the existence of NO in the exhaust gas is very small and within the range of dispersion of the output characteristic of each sensor.

|  | Sensitivity Coefficient (mA/%) | | | | |
|---|---|---|---|---|---|
|  | $O_2$ | CO | $H_2$ | HC | NO |
| Sensor A | +0.4~ +0.8 | −0.2~ −0.4 | −1.0~ −1.5 | −1.2~ −2.4 | 0 |
| Sensor B | +0.4~ +0.8 | −0.2~ −0.4 | −1.0~ −1.5 | −1.2~ −2.4 | +0.2~ +0.4 |

However, according to the following theory of the present invention the NO concentration can be determined from the outputs of the sensors A and B without need of measuring the sensitivity coefficient for NO.

As to the sensitivity coefficients of the sensors A and B, the following equations (6A) to (6C) hold.

$$\gamma_{CO(A)}/\gamma_{O(A)} = \gamma_{CO(B)}/\gamma_{O(B)} = \eta_{CO} (\text{constant}) \quad (6A)$$

$$\gamma_{H(A)}/\gamma_{O(A)} = \gamma_{H(B)}/\gamma_{O(B)} = \eta_H (\text{constant}) \quad (6B)$$

$$\gamma_{HC(A)}/\gamma_{O(A)} = \gamma_{HC(B)}/\gamma_{O(B)} = \eta_{HC} (\text{constant}) \quad (6C)$$

In these equations the subscripts are as noted hereinbefore, and the sensitivity coefficient ratios $\eta_{CO}$, $\eta_H$ and $\eta_{HC}$ are absolute numbers.

Substituting the equations 6(A), 6(B) and 6(C) into the equations (4) and (5), the equations (7) and (8) are obtained.

$$I_{P(A)} = \gamma_{O(A)}(X_O + X_{CO}\eta_{CO} + X_H\eta_H + X_{HC}\eta_{HC}) + \alpha_{(A)} \quad (7)$$

$$I_{P(B)} = \gamma_{O(B)}(X_O + X_{CO}\eta_{CO} + X_H\eta_H + X_{HC}\eta_{HC}) + X_{NO}\gamma_{NO} + \alpha_{(B)} \quad (8)$$

The equations (7) and (8) are rewritten into equations (9) and (10), respectively, wherein $K = X_O + X_{CO}\eta_{CO} + X_H\eta_H + X_{HC}\eta_{HC}$.

$$I_{P(A)} = \gamma_{O(A)} \cdot K + \alpha_{(A)} \quad (9)$$

$$I_{P(B)} = \gamma_{O(B)} \cdot K + X_{NO}\gamma_{NO} + \alpha_{(B)} \quad (10)$$

Eliminating K from the equations (9) and (10) and rearranging these equations with respect to $X_{NO}$, the equation (11) is obtained.

$$X_{NO} = [(I_{P(B)} - \alpha_{(B)}) - (\gamma_{O(B)}/\gamma_{O(A)}) \times (I_{P(A)} - \alpha_{(A)})]/\gamma_{NO} \quad (11)$$

Since the following equation (12) holds, the equation (13) is obtained by substituting the equation (12) into the equation (11).

$$\gamma_{NO(B)}/\gamma_{O(B)} = \eta_{NO} (\text{constant}) \quad (12)$$

$$X_{NO} = [(I_{P(B)} - \alpha_{(B)}) - (\gamma_{O(B)}/\gamma_{O(A)}) \times (I_{P(A)} - \alpha_{(A)})]/\eta_{NO}\gamma_{O(B)} \quad (13)$$

The equation (13) shows that by preliminarily measuring the sensitivity coefficients of the sensors A and B for oxygen, $\gamma_{O(A)}$ and $\gamma_{O(B)}$, and the zero-state outputs of the respective sensors, $\alpha_{(A)}$ and $\alpha_{(B)}$, the NO concentration, $X_{NO}$, can be determined by computation using the measured outputs $I_{P(A)}$ and $I_{P(B)}$ of the sensors A and B. The sensitivity coefficient ratio $\eta_{NO}$ is a constant specific to the employed sensor and can be found in advance. Using the equation (13) it is possible to accurately determine the NO concentration even though the concentration is very low ($10^3$ ppm or below as mentioned above). The preliminary testing is simple since it suffices to find the sensitivity coefficients of the respective sensors only for $O_2$. In the sensor B the reference voltage $V_E$ is relatively high so that the partial pressure of oxygen in the gas diffusion chamber of the sensor B is low ($10^{-8}$ to $10^{-9}$ atm). Therefore, the zero-stage output $\alpha_{(B)}$ of the sensor B is nearly zero. In practice it is permissible to assume that $\alpha_{(B)}=0$ in the equation (13). In the present invention it is not indispensable to use two sensor units. As described hereinbefore, it is also possible to use a single sensor unit to obtain two different output currents respectively corresponding the outputs $P_{I(A)}$ and $P_{I(B)}$ of the sensors A and B in the above description.

The nitrogen oxide as the object of measurement is not limited to NO which is taken as an example in the foregoing description of the theory and also in the following description of the embodiments of the invention. It is also possible to measure the concentration of a different nitrogen oxide such as $NO_2$ or $NO_3$ by selecting a suitable catalyst for decomposing that nitrogen oxide under low partial pressure of coexisting oxygen.

Figure 11:
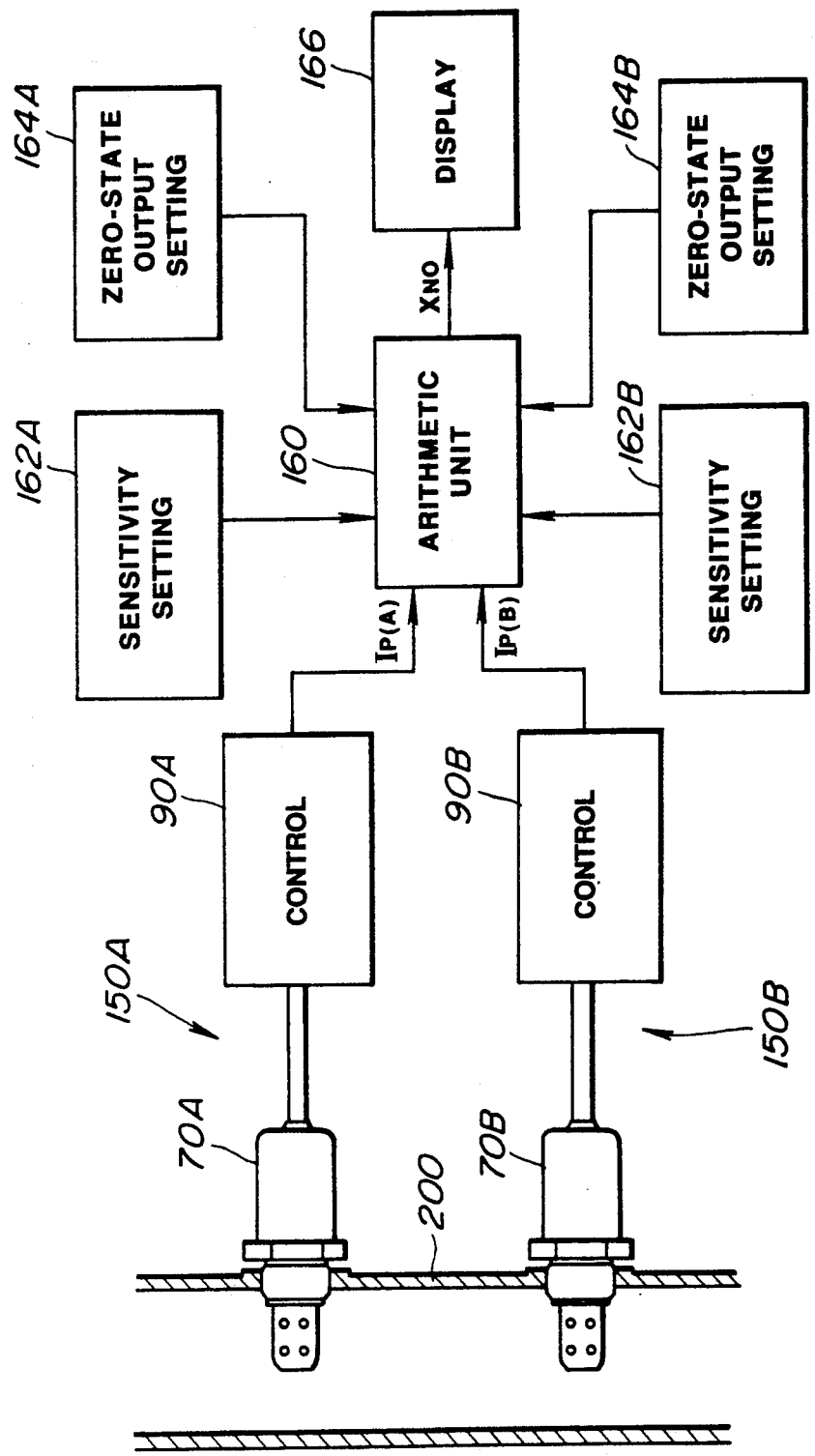
FIG. 11 is a partly diagrammatic illustration of a first embodiment of the invention.
Figure 12A:
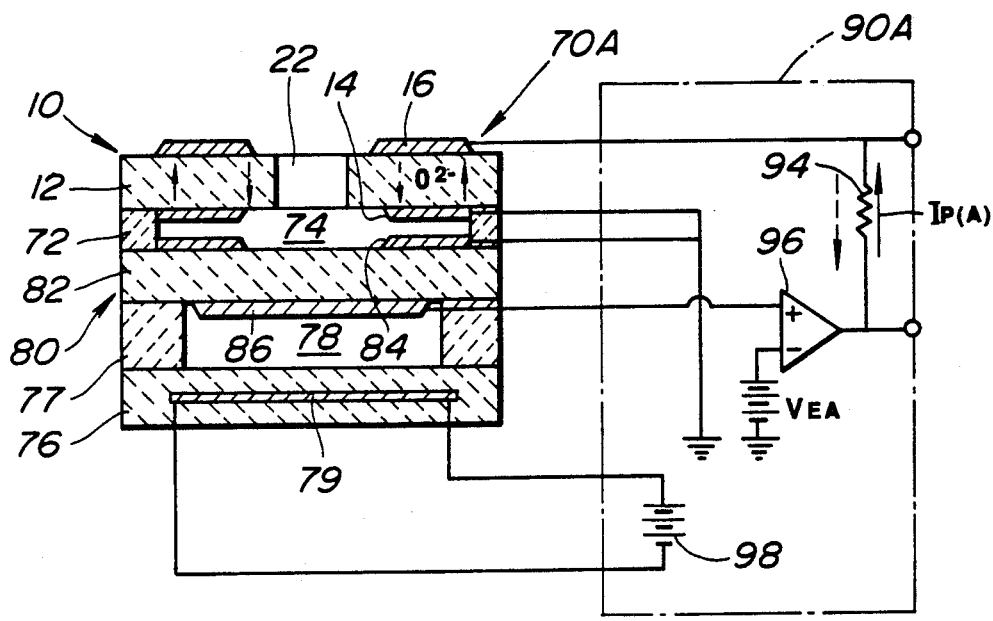
FIGS. 12(A) and 12(B) are partly sectional and partly diagrammatic illustrations of a pair of sensors in the device of FIG. 11.
Figure 12B:
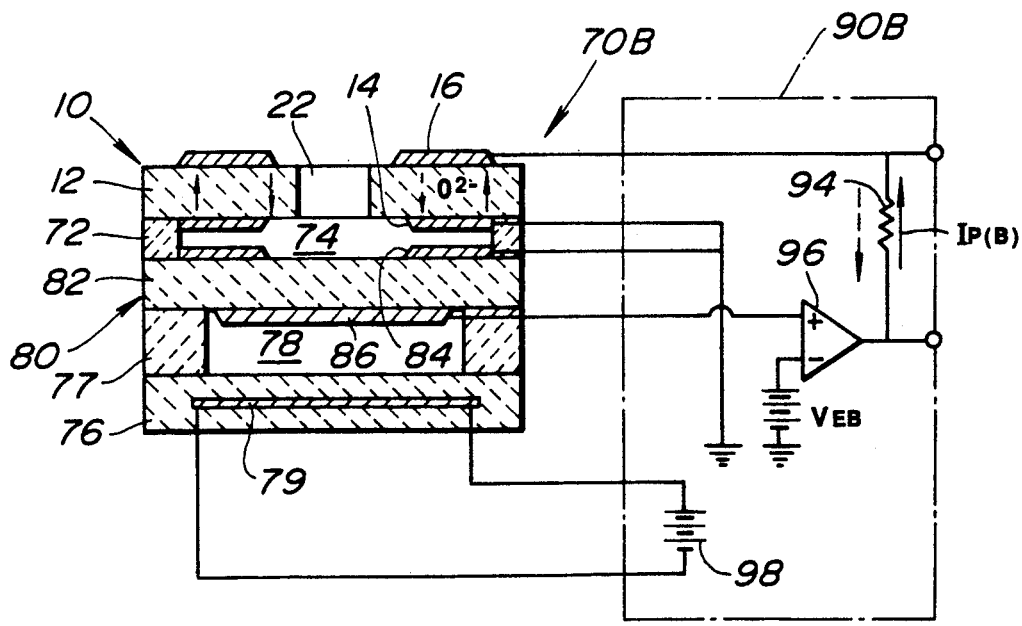

As a first embodiment of the invention, FIGS. 11, 12(A) and 12(B) show a device for measuring the concentration of NO in the exhaust gas of an automotive engine. This embodiment corresponds to the device of FIG. 3.

As shown in FIG. 11 the device has two sensors 150A and 150B each of which is a combination of a gas sensor element 70A, 70B and a control circuit 90A, 90B. The sensor elements 70A and 70B are fitted into an exhaust pipe 200. The distance between the two sensor elements 70A and 70B is made as short as possible. As shown in FIGS. 12(A) and 12(B), the two sensor elements 70A and 70B are almost identical in construction with each other and with the sensor element 70 in FIG. 5. The second sensor element 70B differs from the sensor element 70 in FIG. 5 only in the following two points. In the sensor element 70B the measurement electrode 84 of the sensing cell 80 are made of platinum, which serves as a catalyst for decomposing NO when the partial pressure of coexisting oxygen is low, and hence the separate provision of the catalyst 18 in FIG. 5 is omitted. The sensor element 70B is provided with an electric heater 79 embedded in the shield plate 76. The first sensor element 70A differs from the second sensor element 70B only in that the electrode 14 of the pumping cell 10 and the electrode 84 of the sensing cell 80 do not use platinum and comprise a material which does not decompose NO irrespective of the partial pressure of coexisting oxygen. For example, such a material can be selected from compound oxides of the perovskite structure, such as lanthanum-strontium-iron oxides $La_{1-x}Sr_xFeO_3$, and compound oxides of the fluorite structure, such as $(CeO_2)_{0.6}(LaO_{1.5})_{0.4}$. Since the catalytic materials for the two sensor elements 70A, 70B are as described above, both of these sensor elements are operated so as to maintain a low partial pressure of oxygen in the gas diffusion chambers 74. That is, in this device the reference voltage $V_{EA}$ in the control circuit 90A of the first sensor 150A can be made equivalent to the reference voltage $V_{EB}$ in the second sensor 150B. For example, both $V_{EA}$ and $V_{EB}$ are set at 0.4 V. In each control circuit numeral 98 indicates a power supply for the heater 79.

Figure 13:
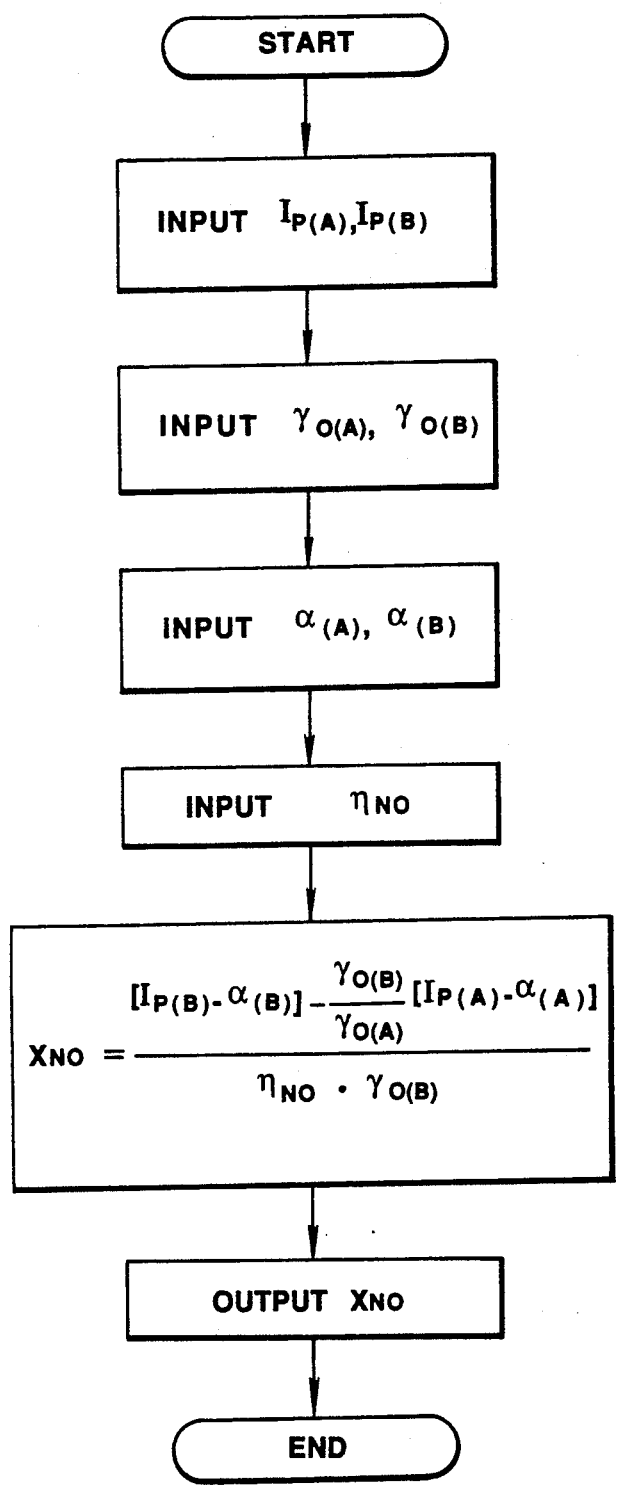
FIG. 13 is a flow chart showing the operations of the arithmetic unit in the device of FIG. 11.

The device of FIG. 11 includes an arithmetic unit 160 comprising a microcomputer to which the outputs $I_{P(A)}$ and $I_{P(B)}$ of the two sensors 150A and 150(B) are inputted. Besides, the device has a pair of sensitivity setting means 162A and 162B to input the sensitivity coefficients of the respective sensors 150A and 150B for oxygen, $\gamma_{O(A)}$ and $\gamma_{O(B)}$, to the arithmetic unit 160. The coefficients $\gamma_{O(A)}$ and $\gamma_{O(B)}$ are determined in advance. Further, there are a pair of zero-state output setting means 164A and 164B to input the zero-state outputs of the respective sensors 150A and 150B, viz. $\alpha_{(A)}$ and $\alpha_{(B)}$, to the arithmetic unit 160. By using these input data and the equation (13) the arithmetic unit 160 makes computation of the concentration of NO in the exhaust gas, $X_{NO}$, in the way as shown in the flow chart of FIG. 13. The NO concentration determined by the computation is transmitted to an output device 166 such as an analog or digital display.

In this embodiment, the data to be prepared in advance are only the sensitivity coefficient of each sensor 150A, 150B for oxygen and the zero-state output of each sensor. Irrespective of the sensitivity coefficients and zero-state outputs of the two sensors 150A and 150B it is possible to accurately determine the NO concentration by using a pair of sensors 150A and 150B having similar characteristics except the difference in the catalytic materials. Since a low partial pressure of oxygen is maintained in the sensor elements 70A, 70B of the both sensors 150A, 150B, it is permissible to assume that the zero-state outputs of the respective sensors to be zero (in the equation (13) $\alpha_{(A)}=0$ and $\alpha_{(B)}=0$).

The device of FIG. 11 can be made very compact and portable and, hence, can easily be installed on automobiles. By using this device the measurement of NO concentrations can be made not only as a bench test but also as a road test on industrially manufactured cars. Compared with the conventional devices for measuring NO concentrations, this device is excellent in responsiveness since the sensor elements are directly fitted into the exhaust pipe without introducing the exhaust gas into a separate container for sampling. The sensor elements 70A, 70B in FIG. 11 are almost similar to the sensor elements of conventional wide-range air/fuel ratio detectors and, hence, can be produced by a process for producing the conventional sensor elements except the changes in the materials of the electrodes 14 and 82. Therefore, the sensor elements 70A and 70B can be produced at relatively low cost. In this embodiment it is unnecessary to use expensive platinum as the material of the electrodes 14 and 84, whereby the cost is further reduced. In this embodiment a low partial pressure is maintained in the both sensor elements 70A and 70B. By virtue of stableness of such a low partial pressure of oxygen the measurement of NO concentrations can be accomplished with high accuracy.

Figure 14:
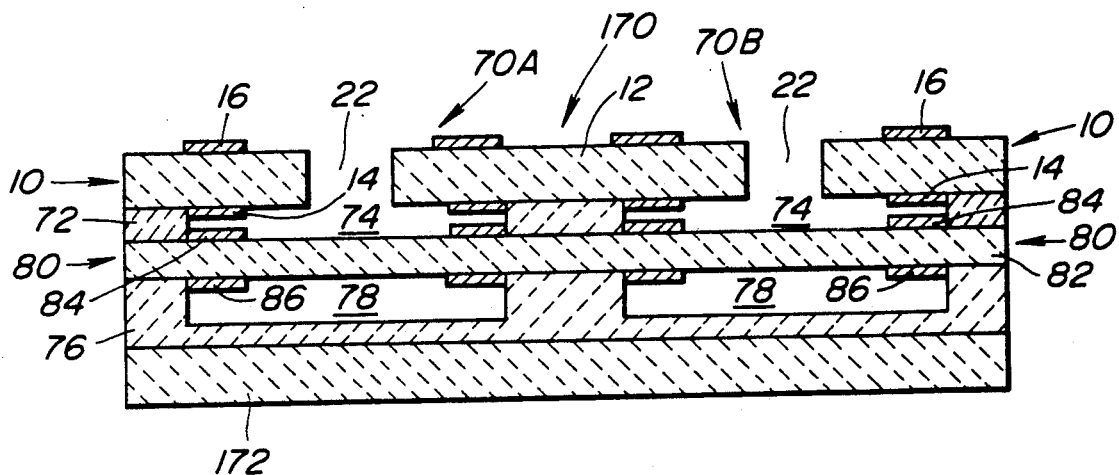
FIG. 14 is a sectional view of a sensor element which is an integration of identical two elements and is used in a second embodiment of the invention.

FIGS. 14–17 show a second embodiment of the invention, which corresponds to the device of FIG. 2. This device has two gas sensor elements 70A and 70B each of which is fundamentally similar to the sensor element 70 in FIG. 5, but as shown in FIG. 14 the two sensor elements 70A and 70B are integrated into a single probe unit 170 on a single substrate 172 of alumina.

Figure 18:
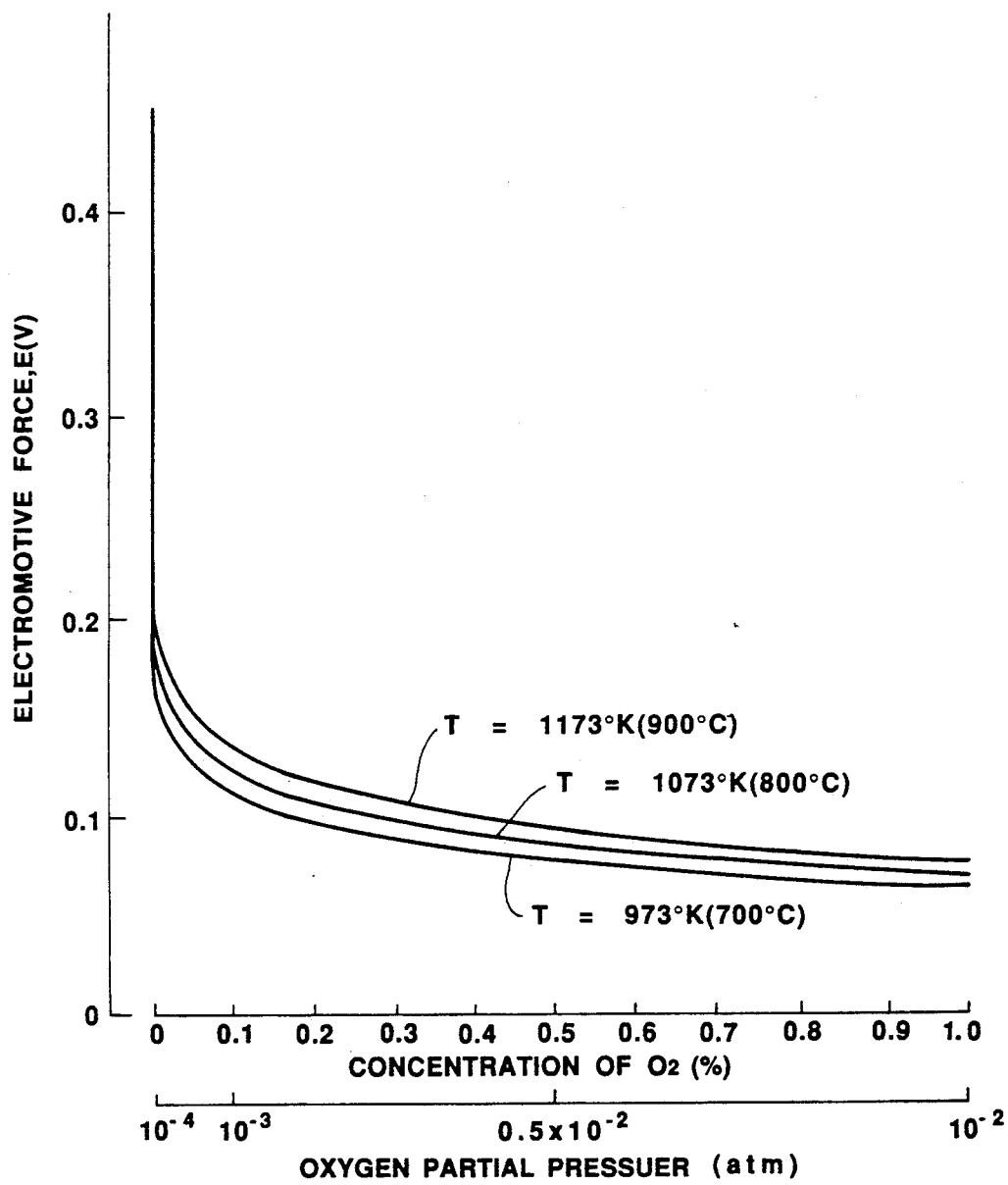
FIG. 18 is a graph showing changes in the output characteristic of an oxygen concentration cell in the sensor element of FIG. 14 with gas temperatures.

When two separate sensor elements are used in combination as in the first embodiment the outputs of the respective sensor elements are possibly differently influenced by the tempera-ture, pressure and flow velocity of the exhaust gas subject to measurement, and hence the accuracy of measurement of the NO concentration might be adversely affected by changes in such environmental conditions even though a pair of sensor elements having similar characteristics are used. For example, FIG. 18 shows the influence of the gas temperature on the relationship between the oxygen partial pressure in the vicinity of the measurement electrode 84 of the sensing cell 80 and the electromotive force E generated by the sensing cell 80. It is seen that the influence of the gas temperature is significant when the oxygen partial pressure is relatively high. This means that when the oxygen partial pressure is high the output $(I_P)$ of each sensor in a device according to the invention will possibly change by the influence of the gas temperature irrespectively of the NO concentration. The integration of the two sensor elements into a unitary element is effective for both equalization of the characteristics of the two sensor elements and avoidance of different influences of the conditions of the gas subject to measurement on the respective sensor elements. Consequently the accuracy of measurement of the NO concentration can further be enhanced. Besides, the sensor elements become more compact by the integration.

Figure 15:
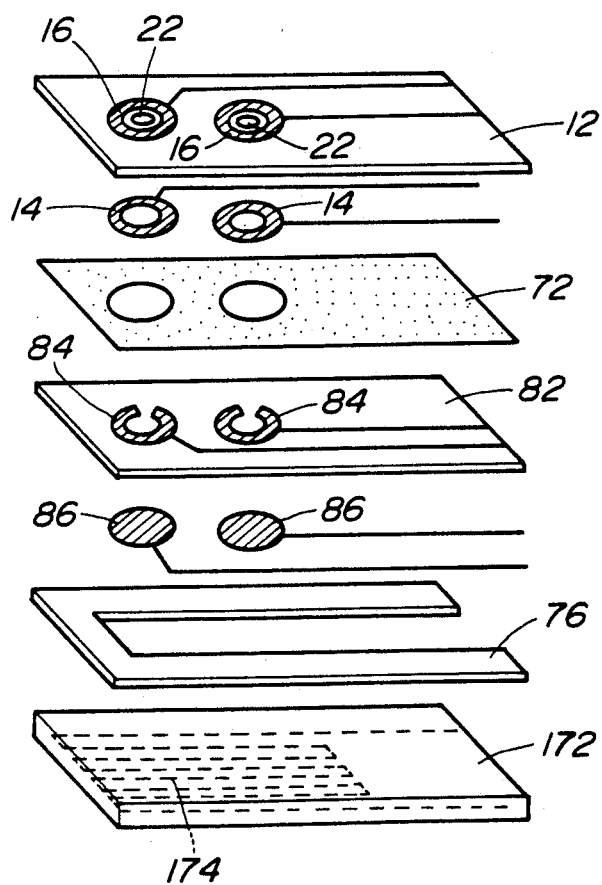
FIG. 15 is an exploded view of the sensor element of FIG. 14.
Figure 16:
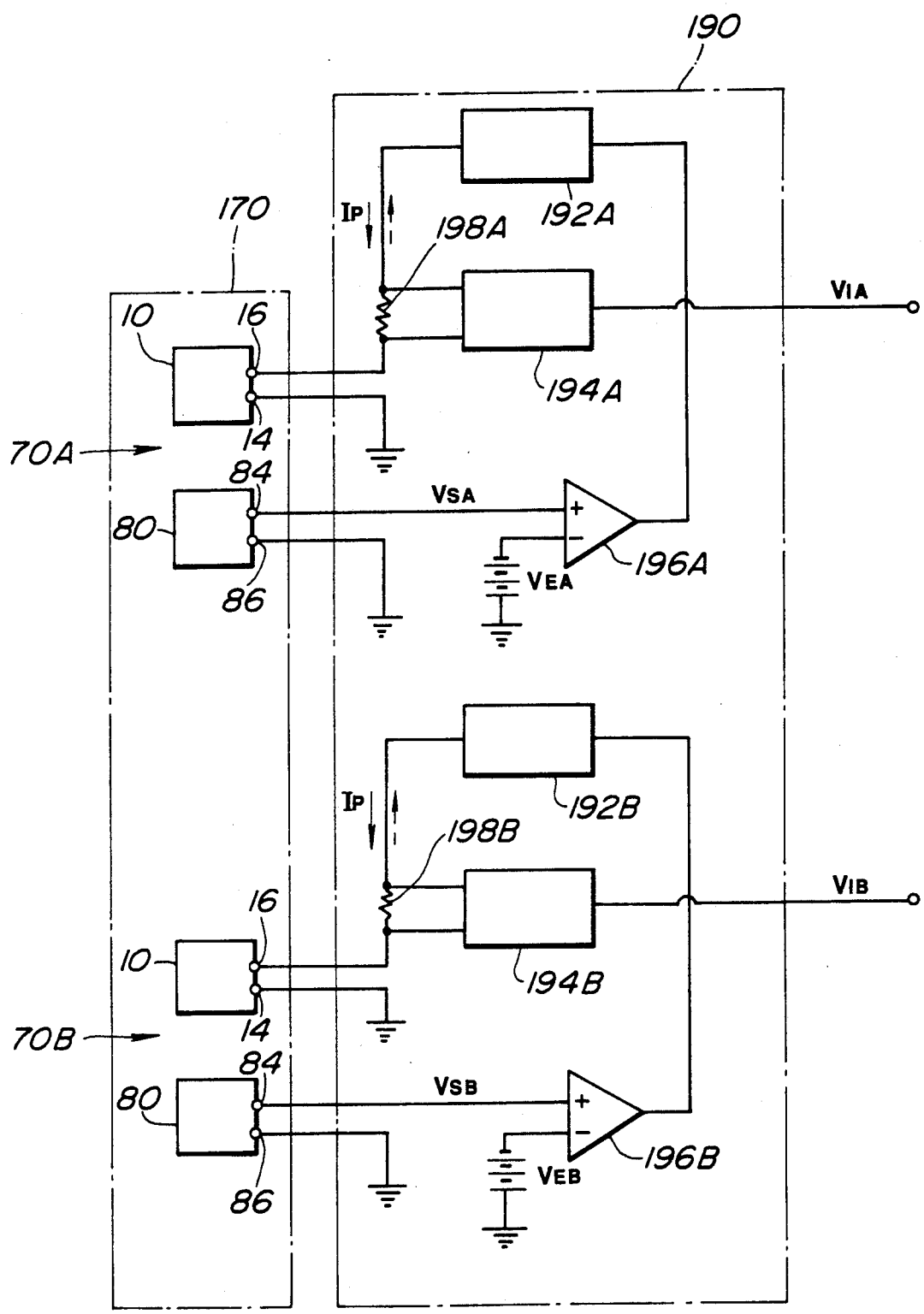
FIG. 16 is a diagram of a control circuit for the sensor element of FIG. 14.

FIG. 15 shows the parts of the integrated probe 170 of FIG. 14. Numeral 174 indicates an electric heater embedded in the alumina substrate 172. The process of producing the probe 170 will be understood from FIG. 15.

In this embodiment, the measurement electrode 84 of each of the two sensor elements 70A, 70B is made of platinum, which acts as a catalyst for decomposing NO when the partial pressure of coexisting oxygen is low. Accordingly, in the sensor control circuit 190 shown in FIG. 16 the reference voltage $V_{EA}$ for the first sensor element 70A is set at a relatively low level (0.1 V), whereas the reference voltage $V_{EB}$ for the second sensor element 70B is set at a relatively high level (0.4 V). In this embodiment the polarity of the reference voltages $V_{EA}$, $V_{EB}$ is reverse to that in the first embodiment (FIGS. 12(A), 12(B)), but this is not important insofar as each reference voltage is inputted to each differential amplifier 96A, 96B at its negative input terminal.

The control circuit 190 has a current supplying means 192A to supply a pumping current $I_P$ to the first sensor element 70A, another current supplying means 192B for the second sensor element 70B, a combination of a resistor 198A and a voltage measuring means 194A to transform the output current $I_{P(A)}$ of the first sensor into an output voltage $V_{IA}$ and another combination of a resistor 198B and a voltage measuring means 194B to transform the output current $I_{P(B)}$ of the second sensor into an output voltage $V_{IB}$.

For stably maintaining the predetermined partial pressure of oxygen in the chamber 74 of each sensor element 70A, 70B it is effective to take some measures such as keeping the temperature of the probe unit 170 constant, even though the exhaust gas temperature varies (e.g. between 200° and 900° C.), by controlling the voltage applied to the heater 174, and/or measuring the temperature of the probe unit 174 and varying the reference voltages $V_{EA}$, $V_{EB}$ according to the measured temperature.

Figure 17:
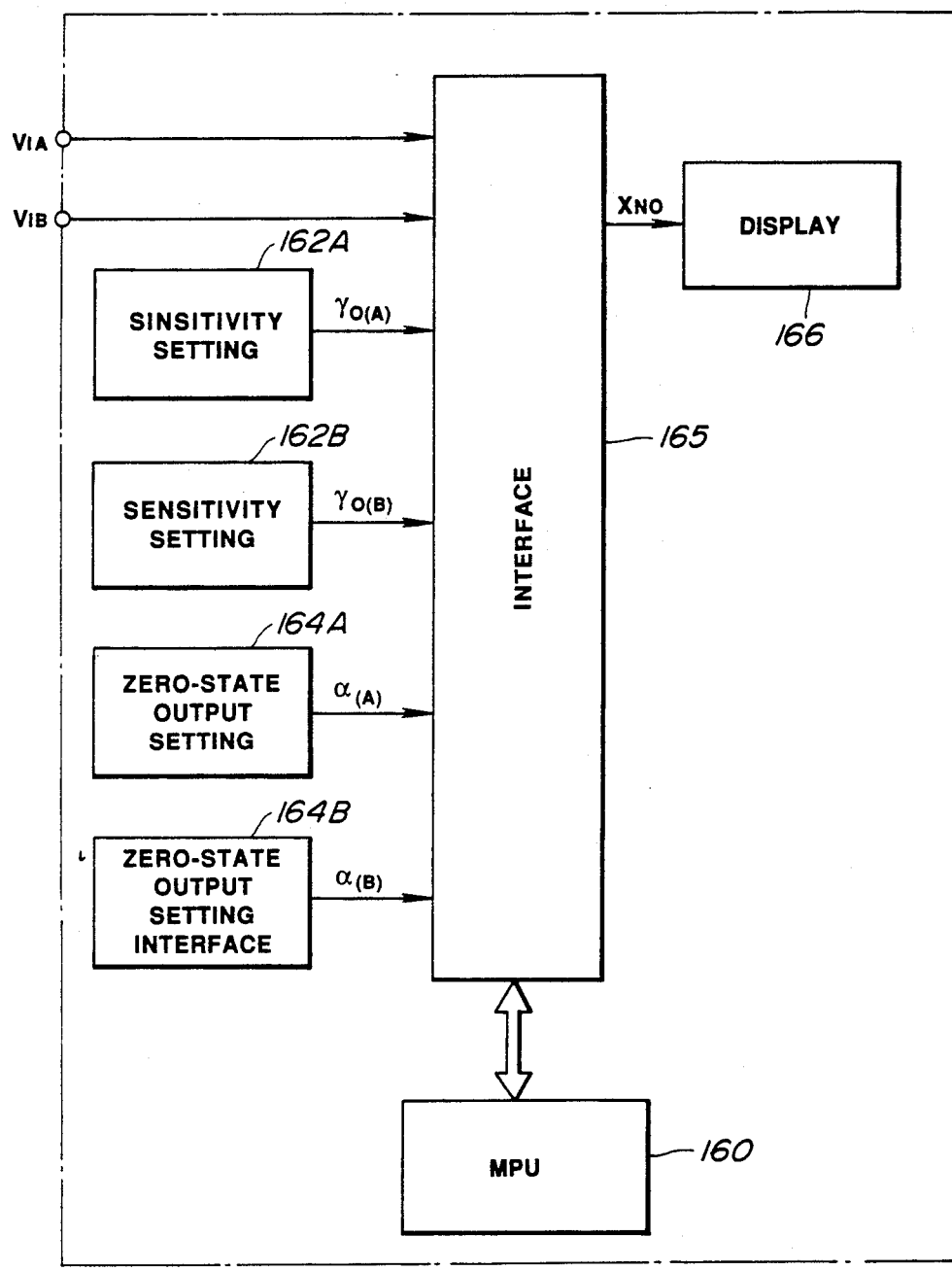
FIG. 17 is a block diagram of an arithmetic unit used in combination with the control circuit of FIG. 16.

FIG. 17 shows the output part of the second embodiment. The principal element is a microprocessor 160 as an arithmetic unit for making computation of the NO concentration according to the equation (13). The output voltages $V_{IA}$ and $V_{IB}$ of the two sensors are inputted to the microprocessor 160 via an interface 165. Similarly to the output part in FIG. 11, a pair of sensitivity setting means 162A, 162B and a pair of zero-state output setting means 164A, 164B are provided. The computed concentration of NO is outputted to a display 166 via the interface 165.

Figure 19:
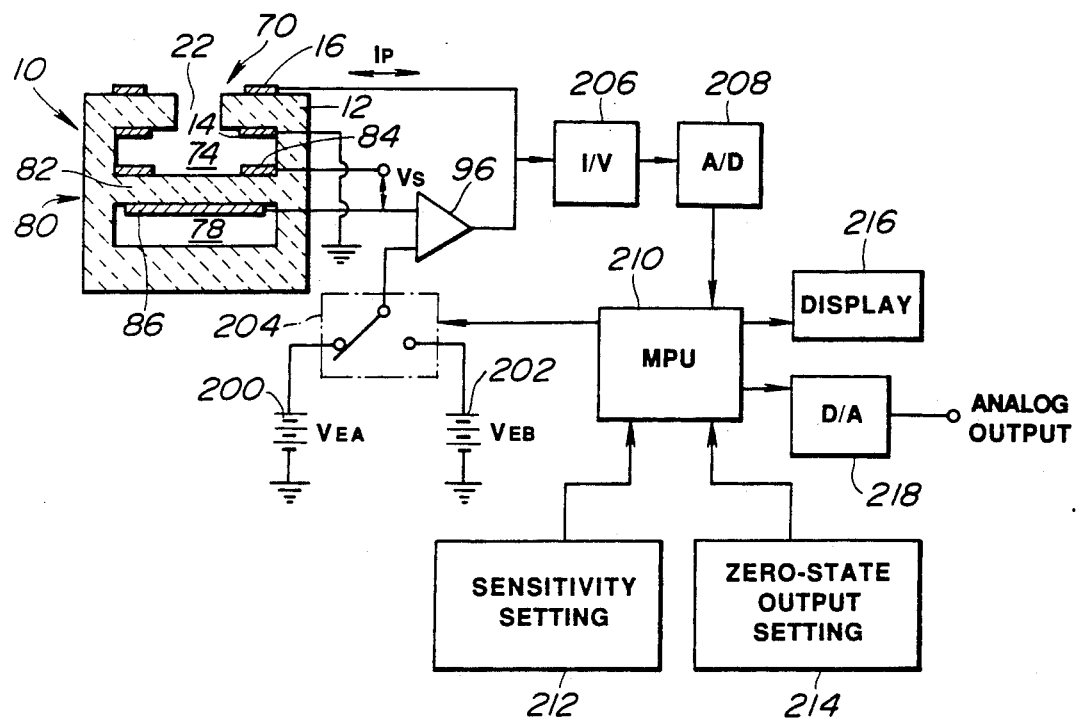
FIG. 19 is a partly sectional and partly diagrammatic illustration of a third embodiment of the invention.

FIG. 19 shows a third embodiment of the invention, which corresponds to the device of FIG. 4.

Figure 20:
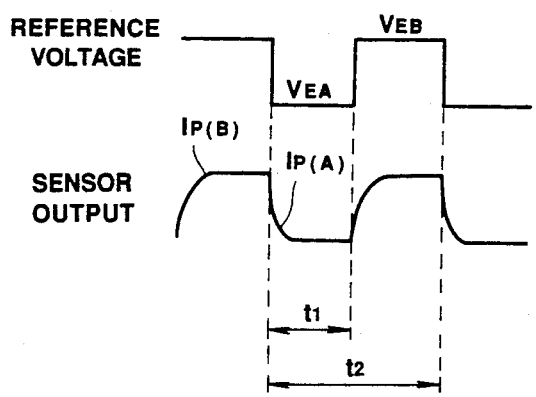
FIG. 20 is a chart showing the manner of time-sharing operation of the device of FIG. 19.

The device of FIG. 19 uses only one sensor element 70 which is fundamentally similar to the element 70 in FIG. 5. The measuring electrode 82 of the sensing cell 80 is made of platinum which acts as a NO decomposing catalyst. The control circuit for the sensor element 70 has a first reference voltage setting means 200 to set a reference voltage $V_{EA}$ at a relatively low level (0.1 V), a second reference voltage setting means 202 to set another reference voltage voltage $V_{EB}$ at a relatively high level (0.4 V) and a switching means 204 to alternately input the two reference voltages $V_{EA}$ and $V_{EB}$ to the differential amplifier 96 at predetermined time intervals. The switching means 204 operates by a signal supplied from a microprocessor 210. The single sensor provides an output $I_{P(A)}$ when the voltage $V_{EA}$ is inputted to the differential amplifier 96 and another output $I_{P(B)}$ when $V_{EB}$ is inputted. The manner of the switchover is shown in FIG. 20. Thus, in this embodiment the single sensor is operated by a time-sharing method.

A merit of this embodiment wherein the two outputs $I_{P(A)}$ and $I_{P(B)}$ are produced by the same sensor element is that the accuracy of the measurement is better than in the case of using a pair of sensor elements which may not completely be identical in characteristics. Besides, the sensor element 70 can be made more compact than the integrated element in the second embodiment. However, in respect of responsiveness this embodiment is slightly inferior to the foregoing embodiments wherein both $P_{I(A)}$ and $P_{I(B)}$ are continuously detected, because the rise of each output $P_{I(A)}$, $P_{I(B)}$ of the sensor is expressed by a curve of first-order lag of response as shown in FIG. 20. Since the length of time that elapses until the sensor output $P_{I(A)}$ or $P_{I(B)}$ reaches an equilibrium value varies depending on the engine load and the engine revolutions, it is favorable to vary the time interval between the switching operations (for example, $t_1$ or $t_2$ in FIG. 20) according to the engine load and the engine revolutions.

In the device of FIG. 19, the output part includes a current-to-voltage converter 206, analog-to-digital converter 208, microprocessor 210, sensitivity coefficient setting means 212, zero-state output setting means 214, display 216 such as a light-emitting diode display using a digital output of the microprocessor 210 and a digital-to-analog converter 218.

What is claimed is:

1. A device for measuring the concentration of a nitrogen oxide in a combustion gas, comprising:
   an electrochemical cell which comprises a member of an oxygen ion conductive solid electrolyte and first and second electrodes attached to the solid electrolyte member;
   a diffusion rate determining means for diffusing a fraction of the combustion gas, with a predetermined resistance to the gas diffusion, into a space in which the first electrode of the electrochemical cell is exposed;

a catalyst which is provided in or in the vicinity of the first electrode of said cell and which decomposes the nitrogen oxide only when the partial pressure of oxygen coexisting with the nitrogen oxide is lower than a predetermined level;

means for supplying a variable DC current to said electrochemical cell to flow in the solid electrolyte between the first and second electrodes to thereby cause migration of oxygen ions in a predetermined direction through the solid electrolyte between the first and second electrodes for adjusting the partial pressure of oxygen in the vicinity of the first electrode of said cell;

means for detecting the partial pressure of oxygen in the vicinity of the first electrode of said cell;

a discriminating means for deciding whether the detected partial pressure of oxygen is lower than said predetermined level or not;

a first current measuring means for measuring the current supplied to said electrochemical cell when it is decided that the detected partial pressure of oxygen is not lower than said predetermined level;

a second current measuring means for measuring the current supplied to said electrochemical cell when it is decided that the detected partial pressure of oxygen is lower than said predetermined level; and means for computing the concentration of the nitrogen oxide in the combustion gas by using the two current values measured by the first and second current measuring means, respectively, the relationship between the concentration of oxygen in said gas and the current measured by the first current measuring means, and the relationship between said concentration of oxygen and the current measured by said second current measuring means, according to the following equation:

$$X_{NO}=[(I_{P(B)}-\alpha_{(B)})-(\gamma_{O(B)}/\gamma_{O(A)})\times(I_{P(A)}-\alpha_{(A)})]/\eta_{NO}\gamma_{O(B)}$$

where $X_{NO}$ is the concentration of the nitrogen oxide, $I_{P(A)}$ is the current measured by the first current measuring means, $I_{P(B)}$ is the current measured by the second current measuring means, $\alpha_{(A)}$ is a current measured by the first current measuring means when the device is operated in a reference gas containing neither oxygen nor the nitrogen oxide, $\alpha_{(B)}$ is a current measured by the second current measuring means when the device is operated in said reference gas, $\gamma_{O(A)}$ is a predetermined coefficient indicating the ratio of the current measured by the first current measuring means to the concentration of oxygen in the combustion gas, $\gamma_{O(B)}$ is a predetermined coefficient indicating the ratio of the current measured by the second current measuring means to the concentration of oxygen in the combustion gas, and $\eta_{NO}$ is a constant.

2. A device according to claim 1, wherein said means for detecting the partial pressure of oxygen comprises an oxygen concentration cell comprising a plate of an oxygen ion conductive solid electrolyte, a measurement electrode on one side of the solid electrolyte plate and a reference electrode on the opposite side of the solid electrolyte plate, the concentration cell being arranged such that said measurement electrode is exposed in said space and located in the vicinity of said first electrode of said electrochemical cell while said reference electrode is exposed to a reference gas.

3. A device according to claim 2, wherein said discriminating means comprises means for detecting the output voltage of said concentration cell and comparing the detected output voltage with at least one reference voltage.

4. A device according to claim 2, wherein said electrochemical cell and said concentration cell are united into a single element such that said space is defined between the solid electrolyte member of said electrochemical cell and the solid electrolyte plate of said concentration cell.

5. A device according to claim 1, wherein said catalyst is selected from the group consisting of platinum and rhodium.

6. A device for measuring the concentration of a nitrogen oxide in a combustion gas, comprising:

first and second electrochemical cells each of which comprises a member of an oxygen ion conductive solid electrolyte and first and second electrodes attached to the solid electrolyte member;

a first diffusion rate determining means for diffusing a fraction of the combustion gas, with a predetermined resistance to the gas diffusion, into a first space in which the first electrode of the first electrochemical cell is exposed;

a second diffusion rate determining means for diffusing a fraction of the combustion gas, with a predetermined resistance to the gas diffusion, into a second space in which the first electrode of the second electrochemical cell is exposed;

a catalyst which is provided in or in the vicinity of the first electrode of each of the first and second electrochemical cells and which decomposes the nitrogen oxide only when the partial pressure of oxygen coexisting with the nitrogen oxide is lower than a predetermined level;

first and second current supplying means for supplying a variable DC current to the first and second electrochemical cells, respectively, to flow in the solid electrolyte between the first and second electrodes to thereby cause migration of oxygen ions through the solid electrolyte between the first and second electrodes;

a first control means for detecting the partial pressure of oxygen in the vicinity of the first electrode of the first electrochemical cell and controlling the current supplied to the first cell such that the detected partial pressure of oxygen becomes constant and higher than said predetermined level;

a first current measuring means for measuring the current supplied to the first electrochemical cell while the partial pressure of oxygen detected by said first control means is higher than said predetermined level;

a second control means for detecting the partial pressure of oxygen in the vicinity of the first electrode of the second electrochemical cell and controlling the current supplied to the second cell such that the detected partial pressure of oxygen becomes constant and lower than said predetermined level;

a second current measuring means for measuring the current supplied to the second electrochemical cell while the partial pressure of oxygen detected by said second control means is lower than said predetermined level; and means for computing the concentration of the nitrogen oxide in the combustion gas by using the two current values measured by the first and second current measuring means, respectively, the relationship between the concentration of oxygen in said gas and the current measured by the first current measuring means, and the relationship between said concentration of oxygen and the current measured by the second current measuring means, according to the following equation:

$$X_{NO} = [(I_{P(B)} - \alpha_{(B)}) - (\gamma_{O(B)}/\gamma_{O(A)}) \times (I_{P(A)} - \alpha_{(A)})]/\eta_{NO}\gamma_{O(B)} \quad (I)$$

where $X_{NO}$ is the concentration of the nitrogen oxide, $I_{P(A)}$ is the current measured by the first current measuring means, $I_{P(B)}$ is the current measured by the second current measuring means, $\alpha_{(A)}$ is a current measured by the first current measuring means when the device is operated in a reference gas containing neither oxygen nor the nitrogen oxide, $\alpha_{(B)}$ is a current measured by the second current measuring means when the device is operated in said reference gas, $\gamma_{O(A)}$ is a predetermined coefficient indicating the ratio of the current measured by the first current measuring means to the concentration of oxygen in the combustion gas, $\gamma_{O(B)}$ is a predetermined coefficient indicating the ratio of the current measured by the second current measuring means to the concentration of oxygen in the combustion gas, and $\eta_{NO}$ is a constant.

7. A device according to claim 6, wherein said first and second control means respectively comprise first and second oxygen concentration cells each of which comprises a plate of an oxygen ion conductive solid electrolyte, a measurement electrode on one side of the solid electrolyte plate and a reference electrode on the opposite side of the solid electrolyte plate, the first concentration cell being arranged such that its measurement electrode is exposed in said first space and located in the vicinity of the first electrode of said first electrochemical cell, the second concentration cell being arranged such that its measurement electrode is exposed in said second space and located in the vicinity of the first electrode of said second electrochemical cell.

8. A device according to claim 7, wherein said first electrochemical cell and said first concentration cell are united into a single element such that said first space is defined between the solid electrolyte member of said first electrochemical cell and the solid electrolyte plate of said first concentration cell, said second electrochemical cell and said second concentration cell being united into a single element such that said second space is defined between the solid electrolyte member of said second electrochemical cell and the solid electrolyte plate of said second concentration cell.

9. A device according to claim 8, wherein the united combination of said first electrochemical cell with said first concentration cell and the united combination of said second electrochemical cell with said second concentration cell are integrated on a substrate into a single part.

10. A device acccording to claim 7, wherein each of the first and second control means comprises means for comparing the output voltage of the assigned one of said first and second concentration cells with a reference voltage for controlling the current supplied to the assigned electrochemical cell so as to keep said output voltage equal to the reference voltage.

11. A device according to claim 6, wherein said catalyst is selected from the group consisting of platinum and rhodium.

12. A device for measuring the concentration of a nitrogen oxide in a combustion gas, comprising:

an electrochemical cell which comprises a member of an oxygen ion conductive solid electrolyte and first and second electrodes attached to the solid electrolyte member;

a diffusion rate determining means for diffusing a fraction of the combustion gas, with a predetermined resistance to the gas diffusion, into a space in which the first electrode of the electrochemical cell is exposed;

a catalyst which is provided in or in the vicinity of the first electrode of said cell and decomposes the nitrogen oxide only when the partial pressure of oxygen coexisting with the nitrogen oxide is lower than a predetermined level;

means for supplying a variable DC current to said electrochemical cell to flow in the solid electrolyte between the first and second electrodes to thereby cause migration of oxygen ions in a predetermined direction through the solid electrolyte between the first and second electrodes for adjusting the partial pressure of oxygen in the vicinity of the first electrode of said cell;

a first reference means for producing a first electrical signal which represents a relatively high first reference partial pressure;

a second reference means for producing a second electrical signal which represents a relatively low second reference partial pressure;

a control means for detecting the partial pressure of oxygen in the vicinity of the first electrode of said electrochemical cell and controlling the current supplied to the electrochemical cell such that the detected partial pressure of oxygen becomes constant and higher than said predetermined level while said first electrical signal is supplied to the control means and becomes constant and lower than said predetermined level while said second electrical signal is supplied to the control means;

a switching means for alternately supplying said first electrical signal and said second electrical signal to said control means at predetermined time intervals;

a current measuring means for measuring the current supplied to said electrochemical cell while the partial pressure of oxygen detected by said control means is higher than said predetermined level and also while the partial pressure detected by said control means is lower than said predetermined level; and means for computing the concentration of the nitrogen oxide in the combustion gas by using the current value measured by said current measuring means while the detected partial pressure of oxygen is higher than said predetermined level, the current value measured by said current measuring means while the detected partial pressure of oxygen is lower than said predetermined level, the relationship between the concentration of oxygen in the gas and the current measured by said current measuring means while the detected partial pressure of oxygen is higher than said predetermined level, and the relationship between said concentration of oxygen and the current measured by said current measuring means while the detected partial pressure of oxygen is lower than said predetermined level, according to the following equation:

$$X_{NO}=[(I_{P(B)}-\alpha)-(\gamma_{O(B)}/\gamma_{O(A)})\times(I_{P(A)}-\alpha)]/\eta_{NO}\cdot\gamma_{O(B)} \quad (II)$$

where $X_{NO}$ is the concentration of the nitrogen oxide, $I_{P(A)}$ is the current measured by the current measuring means while the detected partial pressure of oxygen is higher than said predetermined level, $I_{P(B)}$ is the current measured by the current measuring means while the detected partial pressure of oxygen is lower than said predetermined level, $\alpha$ is a current measured by the current measuring means when the device is operated in a reference gas containing neither oxygen nor the nitrogen oxide, $\gamma_{O(A)}$ is a predetermined coefficient indicating the ratio of the current measured by the current measuring means while the detected partial pressure of oxygen is higher than said predetermined limit to the concentration of oxygen in the combustion gas, $\gamma_{O(B)}$ is a predetermined coefficient indicating the ratio of the current measured by the current measuring means while the detected partial pressure of oxygen is lower than said predetermined limit to the concentration of oxygen in the combustion gas, and $\eta_{NO}$ is a constant.

13. A device according to claim 12, wherein said control means comprises an oxygen concentraion cell comprising a plate of an oxygen ion conductive solid electrolyte, a measurement electrode on one side of the solid electrolyte plate and a reference electrode on the opposite side of the solid electrolyte plate, the concentration cell being arranged such that said measurement electrode is exposed in said space and located in the vicinity of said first electrode of said electrochemical cell while said reference electrode is exposed to a reference gas.

14. A device according to claim 13, wherein said electrochemical cell and said concentration cell are united into a single element such that said space is defined between the solid electrolyte member of said electrochemical cell and the solid electrolyte plate of said concentration cell.

15. A device according to claim 13, wherein each of said first and second electrical signals is a constant voltage signal, said control means comprising means for comparing the output voltage of said concentration cell with either of the first and second voltage signals for controlling the current supplied to the electrochemical cell so as to keep said output voltage equivalent to the compared voltage signal.

* * * * *